(12) United States Patent
Sanner

(10) Patent No.: US 6,284,757 B1
(45) Date of Patent: Sep. 4, 2001

(54) PYRROLO[1,2-A]PYRAZINE DERIVATIVES AS 5HT$_{1A}$ LIGANDS

(75) Inventor: Mark Allen Sanner, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/372,438

(22) Filed: Aug. 11, 1999

Related U.S. Application Data

(60) Provisional application No. 60/096,875, filed on Aug. 17, 1998.

(51) Int. Cl.$^7$ .................................................. A61K 31/495
(52) U.S. Cl. .................................................. 514/249
(58) Field of Search ............................................. 514/249

(56) References Cited

U.S. PATENT DOCUMENTS 5,714,487 * 2/1998 Sanner ................................. 514/249

FOREIGN PATENT DOCUMENTS

| 9723482 | 7/1997 | (WO) . |
| 9743271 | 11/1997 | (WO) . |
| 9808817 | 5/1998 | (WO) . |

OTHER PUBLICATIONS

H. Nissbrandt et al. Naunyn–Schmiedeberg's Arch. Pharmacol. (1992) vol. 346, pp 12–19., "The influence of serotoninergic drugs on dopaminergic neurotransmission in rat substantia nigra, striatum and limbic forebrain in vivo."

P. Meltzer et al. , Bioorganic & Medicininal Chemistry Letter (1999) vol. 9, pp. 857–862, Bicyclo[3.2.1]Octanes: "Synthesis and Inhibition of Binding at the Dopamine and Serotonin Transporters".

Search Report for EP9930 5979, Mar. 22, 2000.

* cited by examiner

*Primary Examiner*—William R. A. Jarvis
(74) *Attorney, Agent, or Firm*—P. C. Richardson; P. H. Ginsburg; A. David Joran

(57) ABSTRACT

This invention relates to the use of compounds of formula I

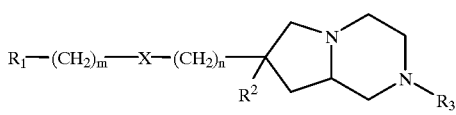

wherein $R_1$, $R_2$, $R_3$, X, m and n are defined as in the specification, and their pharmaceutically acceptable salts, for the treatment of disorders of the serotonin system.

26 Claims, No Drawings

PYRROLO[1,2-A]PYRAZINE DERIVATIVES AS 5HT$_{1A}$ LIGANDS

This application claims priority under 35 U.S.C. §119 from U.S. application Ser. No. 060/096,875, filed Aug. 17, 1998, which application is hereby incorporated by reference.

BACKGROUND OF THE INVENTION

The present invention relates to the use of pharmacologically active 2,7-substituted octahydro-1H-pyrrolo[1,2-a] pyrazine derivatives, and their acid addition salts. The compounds of this invention are ligands for serotonin receptor subtypes, especially the 5HT$_{1A}$ receptor, and are therefore useful in the treatment of disorders that can be treated by altering (i.e., increasing or decreasing), serotonin mediated neurotransmission.

The pharmacologically active 2,7-substituted octahydro-1 H-pyrrolo[1,2-a]pyrazine derivatives of the formula I, as defined below, are also ligands for dopamine receptor subtypes, especially the dopamine D4 receptor. They are useful in treating disorders that can be treated by altering (i.e., increasing or decreasing) dopamine mediated neurotransmission. The dopamine receptor binding activity of such compounds is referred to in World Patent Application WO 97/23482, which designates the United States and was published on Jul. 3, 1997. This application (WO 97/23482) is incorporated herein by reference in its entirety.

Serotonin plays a role in several psychiatric disorders, including anxiety, Alzheimer's disease, depression, nausea and vomiting, eating disorders, and migraine. (See Rasmussen et al., "Chapter 1. Recent Progress in Serotonin (5HT)$_{1A}$ Receptor Modulators", in *Annual Reports in Medicinal Chemistry, Section I*, 30, pp. 1–9, 1995, Academic Press, Inc.; Antigas et al., *Trends Neurosci.*, 19 (9), 1996, pp. 378–383; and Wolf et al., *Drug Development Research*, 40, 1997, pp. 17–34.) Serotonin also plays a role in both the positive and negative symptoms of schizophrenia. (See Sharma et al., Psychiatric Annals., 26 (2), February, 1996, pp. 88–92.)

SUMMARY OF THE INVENTION

This invention relates to a method of treating a disorder that can be treated by altering (e.g., increasing or decreasing) serotonin mediated neurotransmission in a mammal, including a human, comprising administering to such mammal an amount of a compound of formula I

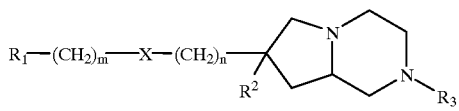

I wherein

R$_1$ is phenyl, naphthyl, benzoxazolonyl, indolyl, indolonyl, benzimidazolyl, quinolyl, furyl, benzofuryl, thienyl, benzothienyl, oxazolyl, benzoxazolyl;

R$_2$ is H or (C$_1$–C$_6$)alkyl;

R$_3$ is phenyl, pyridinyl, pyrimidinyl, pyrazinyl, or pyridazinyl;

R$_4$ is H or (C$_1$–C$_6$)alkyl;

R$_5$ is H or (C$_1$–C$_6$)alkyl;

wherein each group of R$_1$ and R$_3$ may be independently and optionally substituted with one to four substituents independently selected from the groups consisting of fluoro, chloro, bromo, iodo, cyano, nitro, thiocyano, —SR$_4$, —SOR$_4$, —SO$_2$R$_4$, —NHSO$_2$R$_4$, —(C$_1$–C$_6$) alkoxy, —NR$_4$R$_5$, —NR$_4$COR$_5$, —CONR$_4$R$_5$, phenyl, —COR$_4$, —COOR$_4$, —(C$_1$–C$_6$)alkyl substituted with one to six halogens, —(C$_3$–C$_6$)cycloalkyl, and trifluoromethoxy;

X is O, S, SO, SO$_2$, NR$_4$, C=O, CH(OH), CHR$_4$,

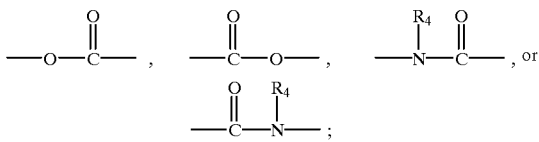

m is 0, 1 or 2; and
n is 0, 1 or 2;
a pharmaceutically acceptable salt thereof;
that is effective in treating such disorder.

In another aspect, this invention relates to any of the foregoing methods of treatment wherein the compound of formula I or pharmaceutically acceptable salt that is employed is one wherein R$_1$ is phenyl, naphthyl, benzoxazolonyl, indolyl, indolonyl, benzimidazolyl, or quinolyl; and wherein R$_1$ and R$_3$ may be independently substituted with up to three substituents independently selected from the group consisting of fluoro, chloro, bromo, iodo, cyano, —NR$_4$R$_5$, —(C$_1$–C$_6$)alkoxy, —COOR$_4$, —CONR$_4$R$_5$, —(C$_1$–C$_6$)alkyl, —(C$_1$–C$_6$)alkyl substituted with one to six halogens, —(C$_3$–C$_6$)cycloalkyl, and trifluoromethoxy;

R$_2$ is H or CH$_3$;
X is O, C=O, CHOH, —C(=O)O—, or CH$_2$,
m is 0 or 1; and
n is 0 or 1.

In another aspect, this invention relates to any of the foregoing methods of treatment wherein the compound of formula I or pharmaceutically acceptable salt that is employed is one wherein R$_1$ is phenyl or substituted phenyl;
R$_3$ is substituted or unsubstituted phenyl, pyridinyl, or pyrimidinyl; and
X is O, —C(=O)O—, or CH$_2$.

In another aspect, this invention relates to any of the foregoing methods of treatment wherein the compound of formula I or pharmaceutically acceptable salt that is employed is one wherein R$_2$ is H;
X is O;
m is 0; and
n is 1.

In another aspect, this invention relates to any of the foregoing methods of treatment wherein the compound of formula I or pharmaceutically acceptable salt that is employed is one wherein R$_1$ is fluorophenyl, cyanophenyl or (trifluoromethyl) phenyl;
R$_3$ is chloropyridinyl.

In another aspect, this invention relates to any of the foregoing methods of treatment wherein the compound of formula I or pharmaceutically acceptable salt that is employed is one wherein R$_1$ is fluorophenyl, cyanophenyl or (trifluoromethyl) phenyl;

R₃ is fluoropyrimidinyl.

In another aspect, this invention relates any of the foregoing methods of treatment wherein the compound of formula I or pharmaceutically acceptable salt that is employed is one wherein R₃ is 5-chloro-2-pyridinyl.

In another aspect, this invention relates any of the foregoing methods of treatment wherein the compound of formula I or pharmaceutically acceptable salt that is employed is one wherein R₃ is 5-fluoro-2-pyrimidinyl.

Examples of preferred methods of this invention are those that employ one of the following compounds of the formula I or a pharmaceutically acceptable salt thereof:

(7S,8aS)-7-(4-fluorophenoxy)methyl-2-(5-chloropyridin-2-yl)-1,2,3,4,6,7,8,8a-octahydro-pyrrolo[1,2-a]pyrazine;

(7S,8aS)-7-(3-cyanophenoxy)methyl-2-(5-chloropyidin-2-yl)-1,2,3,4,6,7,8,8a-octahydro-pyrrolo[1,2-a]pyrazine;

(7S,8aS)-7-(4-fluorophenoxy)methyl-2-(5-fluoropyrimidin-2-yl)-1,2,3,4,6,7,8,8a-octahydro-pyrrolo[1,2-a]pyrazine;

(7S,8aS)-7-(3-(trifluoromethyl)phenoxy)methyl-2-(5-fluoropyrimidin-2-yl)-1,2,3,4,6,7,8,8a-octahydro-pyrrolo[1,2-a]pyrazine;

(7S,8aS)-7-(3-cyanophenoxy)methyl-2-(5-fluoropyrimidin-2-yl)-1,2,3,4,6,7,8,8a-octahydro-pyrrolo[1,2-a]pyrazine;

(7S,8aS)-7-(4-cyanophenoxy)methyl-2-(5-fluoropyrimidin-2-yl)-1,2,3,4,6,7,8,8a-ctahydro-pyrrolo[1,2-a]pyrazine;

The term "treating", as used herein, refers to retarding or reversing the progress of, or lleviating or preventing either the disorder or condition to which the term "treating" applies, or ne or more symptoms of such disorder or condition. The term "treatment", as used herein, refers to the act of treating a disorder or condition, as the term "treating" is defined above.

The chemist of ordinary skill will recognize that certain combinations of substituents included within the scope of formula I may be chemically unstable and will avoid these combinations or alternatively protect sensitive groups with well known protecting groups.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

The compounds of formula I contain one or more chiral centers and therefore exist in different enantiomeric and diasteriomeric forms. Formula I, as defined above, includes, and this invention relates to the use of, all optical isomers and other stereoisomers of compounds of the formula I and mixtures thereof.

This invention also relates to a method of treating a disorder or condition that can be treated by altering (i.e., increasing or decreasing) serotonin mediated neurotransmission in a mammal, including a human, comprising administering to said mammal an amount of a compound of the formula I, as defined above, or a pharmaceutically acceptable salt thereof, that is effective in treating such disorder or condition.

This invention also relates to a method of treating migraine, headache or cluster headache in a mammal, including a human, comprising administering to said mammal an amount of a compound of the formula I, as defined above, or a pharmaceutically acceptable salt thereof, that is effective in treating such disorder.

This invention also relates to a method of treating a disorder selected from, depression (i.e., dysthymia, major depressive disorder, pediatric depression, recurrent depression, single episode depression, post partum depression, depression in Parkinson's patients, cancer patients, and post myocardial infarction patients, and sub-syndromal symptomatic depression) generalized anxiety disorder, panic disorder, obsessive-compulsive disorder, postraumatic stress disorder, avoidant personality disorder, borderline personality disorder and phobias in a mammal, including a human, comprising administering to said mammal an amount of a compound of the formula I, as defined above, or a pharmaceutically acceptable salt thereof, that is effective in treating such disorder.

This invention also relates to a method for treating disorders of cognition, memory or learning, such as age related memory disorder or neurodegenerative diseases such as Alzheimer's disease in a mammal, including a human, comprising administering to said mammal an amount of a compound of the formula I, as defined above, or a pharmaceutically acceptable salt thereof, that is effective in treating such disorder.

This invention also relates to a method for treating attention deficit hyperactivity disorder (ADHD) in a mammal, including a human, comprising administering to said mammal an amount of a compound of the formula I, as defined above, or a pharmaceutically acceptable salt thereof, that is effective in treating such disorder.

This invention also relates to a method of treating an eating disorder (eg., bulimia or anorexia nervosa), or a chemical dependency or addiction, (e.g., a dependency on, or addiction to, alcohol, nicotine, cocaine, heroin, phenolbarbitol or a benzodiazepine), in a mammal, including a human, comprising administering to said mammal an amount of a compound of the formula I, as defined above, or a pharmaceutically acceptable salt thereof, that is effective in treating such disorder.

This invention also relates to a method of treating anxiety or depression associated with senile dementia or Alzheimer's disease in a mammal, including a human, comprising administering to said mammal an amount of a compound of the formula I, as defined above, or a pharmaceutically acceptable salt thereof, that is effective in treating such disorder.

This invention also relates to a method for treating cancer, such as prostrate cancer, in a mammal, including a human, comprising administering to said mammal an amount of a compound of the formula I, as defined above, or a pharmaceutically acceptable salt thereof, that is effective in treating such disorder.

This invention also relates to a method of treating cerebral infarct such as that caused by stroke, ischemia or traumatic head injury in a mammal, including a human, comprising administering to said mammal an amount of a compound of the formula I, as defined above, or a pharmaceutically acceptable salt thereof, that is effective in treating such disorder.

This invention also relates to a method of treating a sexual disorder such as paraphilias, premature ejaculation or sexual dysfunction in a mammal, including a human, comprising administering to said mammal an amount of a compound of the formula I, as defined above, or a pharmaceutically acceptable salt thereof, that is effective in treating such disorder.

This invention also relates to a method of treating dizziness in a mammal, including a human, comprising administering to said mammal an amount of a compound of the formula I, as defined above, or a pharmaceutically acceptable salt thereof, that is effective in treating such disorder.

This invention also relates to a method of treating peptic ulcer in a mammal, including a human, comprising administering to said mammal an amount of a compound of the formula I, as defined above, or a pharmaceutically acceptable salt thereof, that is effective in treating such disorder.

This invention also relates to any of the foregoing methods, wherein the compound of the formula I, as defined above, or pharmaceutically acceptable salt thereof, is administered in combination with a serotonin reuptake inhibitor (SRI) (e.g., sertraline, fluoxetine, fenfluramine, or or fluvoxamine). The term "administered in combination with", as used herein, means that the compound of formula I or pharmaceutically acceptable salt thereof is administered in the form of a pharmaceutical composition that also contains an SRI, or that such compound or salt is administered in a separate pharmaceutical composition from that in which the SRI is administered, but as part of a dose regimen that calls for the administration of both active agents for treatment of a particular disorder or condition.

This invention also relates to the above method of treating cerebral infarct such as that caused by stroke, ischemia or traumatic head injury in a mammal, wherein the compound of the formula I, as defined above, or pharmaceutically acceptable salt thereof, is administered in combination with a serotonin-2 ($5HT_2$) receptor antagonist (e.g., ketanserin, pelanserin, pipamperone, spiperone, pirenperin or ritanserin) or a pharmaceutically acceptable salt thereof. Other $5HT_2$ receptor antagonists that can be used in the methods of this invention are referred to in U.S. Pat. No. 5,364,857, which issued on Nov. 15, 1994. This patent is incorporated herein by reference in its entirety.

The pharmaceutically acceptable acid addition salts of compounds of the formula I may be used, as referred to above, in the various methods of this invention. The compounds of formula I are basic in nature and are capable of forming a wide variety of salts with various inorganic and organic acids. The acids that may be used to prepare pharmaceutically acceptable acid addition salts of those compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

The term "one or more substituents", as used herein, includes from one to the maximum number of substituents possible based on the number of available bonding sites.

The term "disorders of the serotonin system", as referred to herein, refers to disorders, the treatment of which can be effected or facilitated by altering (i.e., increasing or decreasing) serotonin mediated neurotransmission.

Formula I above includes compounds identical to those depicted but for the fact that one or more atoms (for example, hydrogen, carbon or fluorine atoms) are replaced by radioactive isotopes thereof. Such radiolabelled compounds are useful as research and diagnostic tools in, for example, metabolism studies, pharmacokinetic studies and binding assays.

This invention also relates to a method, such as positron emission tomography (PET), of obtaining images of a mammal, including a human, to which a radiolabelled compound of the formula I, or pharmaceutically acceptable salt thereof, has been administered.

The compounds of formula I that are employed in the present invention, being ligands for serotonin receptor subtypes, especially the $5HT_{1A}$ receptor, within the body, are accordingly of use in the treatment of disorders of the serotonin system.

DETAILED DESCRIPTION OF THE INVENTION

The compounds of formula I and their pharmaceutically acceptable salts (hereinafter also referred to, collectively, as "the therapeutic compounds used in the methods of this invention") can be prepared as described in World Patent Application WO 97/23482, which designates the United States and was published on Jul. 3, 1997. This application (WO 97/23482) is incorporated herein by reference in its entirety.

Compounds of formula I in which one or more atoms are radioactive may be prepared by methods known to a person of ordinary skill in the art.

For example, compounds of formula I wherein the radioactive atom is tritium may be prepared by reacting an aryl halide Ar—X, wherein the halogen is chlorine, bromine or iodine, with gaseous $^3H_2$ and a nobel metal catalyst, such as palladium suspended on carbon, in a suitable solvent such as a lower alcohol, perferably methanol or ethanol. Compounds of formula I wherein the radioactive atom is $^{18}F$ may be prepared by reacting an aryl trialkyl stannane Ar-SnR$_3$, wherein R is lower alkyl, preferably methyl or n-butyl, with $^{18}F$-enriched fluorine ($F_2$), $OF_2$ or $CF_2OOF$ in a suitably inert solvent (cf M. Namavari, et at., *J. Fluorine Chem.*, 1995, 74, 113).

Compounds of formula I wherein the radioactive atom is $^{11}C$ or $^{14}C$ may be prepared by reacting an aryl halide Ar—X, wherein X is preferably bromine or iodine, or an aryl trifluoromethane sulfonate (Ar—$OSO_2CF_3$) with potassium [$^{11}C$]cyanide or potassium [$^{14}C$]cyanide and a nobel metal catalyst, preferably tetrakis(triphenylphosphine)palladium, in a reaction inert solvent such water or tetrahydrofuran, and preferably a mixture of water and tetrahydrofuran. (See Y. Andersson, B. Langstrom, *J. Chem. Soc. Perkin Trans.* 1, 1994, 1395).

The utility of radioactive agents with affinity for $5HT_{1A}$ receptors for visualizing organs of the body either directly or indirectly has been documented in the literature. For example, C.-Y. Shiue et al., *Synapse*, 1997, 25, 147 and S. Houle et al, *Can. Nucl. Med. Commun*, 1997, 18, 1130, describe the use of $5HT_{1A}$ receptor ligands to image $5HT_{1A}$ receptors in the human brain using positron emission tomography (PET). The foregoing references are incorporated herein by reference in their entireties.

The therapeutic compounds used in the methods of this invention can be administered orally, buccally, transdermally (e.g., through the use of a patch), parenterally or topically. Oral administration is preferred. In general, these compounds are most desirably administered in dosages ranging from about 1 mg to about 1000 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

When used in the same oral, parenteral or buccal pharmaceutical composition as an SRI, the daily dose of the compound of formula I or pharmaceutically acceptable salt thereof will be within the same general range as specified above for the administration of such compound or salt as a single active agent. The daily dose of the SRI in such a composition will generally be within the range of about 1 mg to about 400 mg.

When used in the same oral, parenteral or buccal pharmaceutical composition as a $5HT_2$ antagonist, the daily dose of the compound of formula I or pharmaceutically acceptable salt thereof will be within the same general range as specified above for the administration of such compound or salt as a single active agent. The daily dose of the $5HT_2$ antagonist in such a composition will generally be within the range of about 0.1–10 parts by weight, relative to 1.0 part by weight of the compound formula I.

The therapeutic compounds used in the methods of this invention may be administered alone or in combination with pharmaceutically acceptable carriers or diluents by either of the two routes previously indicated, and such administration may be carried out in single or multiple doses. More particularly, the therapeutic compounds used in the methods of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, for example. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound used in the methods of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the therapeutic compounds used in the methods of the present invention topically when treating inflammatory conditions of the skin and this may preferably be done by way of creams, jellies, gels, pastes, ointments and the like, in accordance with standard pharmaceutical practice.

The activity of the compounds of the present invention with respect to $5HT_{1A}$ binding ability can be determined according to the following procedure. Binding assays using membranes derived from HeLa cells expressing the human $5HT_{1A}$ receptor or from membranes derived from rat brain tissue can be performed according to standard procedures. For example, HeLa cells expressing the human $5HT_{1A}$ receptor can be grown in culture to confluence and then harvested by replacing the media with phosphate buffered saline containing 5 mM EDTA and centrifuging at 1000×g for 10 minutes at 4° C. The pellet is homogenized in a 50 mM Tris buffer containing 4 mM $CaCl_2$ and having a pH of 7.7, using a Brinkman Polytron at setting 6 for 20 seconds and centrifuged at 48,000×g for 10 minutes at 4° C. Membranes are stored frozen at −78° C. until the time of assay. On the day of the experiment, the membranes are resuspended in a 50 mM Tris buffer (pH 7.7) containing 4 mM $CaCl_2$ and 10 $\mu$M pargyline to a final tissue concentration of 2.5 mg/mL and added to test tubes containing an incubation buffer, various concentrations of test drug, and [$^3$H]-8-OH-DPAT. Non-specific binding is defined in the presence of a saturating concentration of 5HT. Assay tubes are incubated for 30 minutes at 37° C. to attain equilibrium, and incubations are terminated by rapid filtration through Whatman GF/B filters using a Brandel cell harvester. The membranes are washed three times with 4 mL aliquots of an ice-cold buffer (without $CaCl_2$ or pargyline). Membrane-bound ligand is determined by liquid scintillation counting of the filters in Ready-Safe scintillation cocktail. The dissociation constant ($K_d$) for the radioligand, previously determined by saturation analysis, is used to calculate apparent $K_i$'s by means of the Cheng-Prusoff equation (Cheng and Prusoff, 1973). The $IC_{50}$ concentrations (concentration of compound required to displace specific binding by 50%) can be calculated by linear regression analysis of the concentration-response curves from competition binding studies. The preferred compounds of this invention bind to the human $5HT_{1A}$ receptor with a $K_i$ less than 1.0 micromolar.

The agonist and antagonist activities of the therapeutic compounds used in the methods of this invention at $5\text{-}HT_{1A}$ receptors can be determined using a single saturating concentration according to the following procedure. Male Hartley guinea pigs are decapitated and $5\text{-}HT_{1A}$ receptors are dissected out of the hippocampus, while receptors are obtained by slicing at 350 mM on a McIlwain tissue chopper and dissecting out the substantia nigra from the appropriate slices. The individual tissues are homogenized in a 5 mM HEPES buffer containing 1 mM EGTA (pH 7.5) using a hand-held glass-Teflon® homogenizer and centrifuged at 35,000×g for 10 minutes at 4° C. The pellets are resuspended in a 100 mM HEPES buffer containing 1 mM EGTA (pH 7.5) to a final protein concentration of 20 $\mu$g of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 $\mu$M GTP and 0.5–1 microcuries of [$^{32}$P]-ATP (30 Ci/mmol: NEG-003—New England Nuclear). Incubation is initiated by the addition of tissue to siliconized microfuge tubes (in triplicate) at 30° C. for 15 minutes. Each tube receives 20 $\mu$L tissue, 10 $\mu$L drug or buffer (at 10×final concentration), 10 $\mu$L 32 nM agonist or buffer (at 10×final concentration), 20 $\mu$L forskolin (3 $\mu$M final concentration) and 40 $\mu$L of the preceding reaction mix.

Incubation is terminated by the addition of 100 mL 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^2$P]-cAMP is accomplished using the method of Salomon et al., *Analytical Biochemistry*, 1974, 58, 541–548. Radioactivity is quantified by liquid scintillation counting. Maximal inhibition is defined by 10 μg (R)-8-OH-DPAT for 5-HT$_{1A}$ receptors. Percent inhibition by the test compounds is then calculated in relation to the inhibitory effect of (R)-8-OH-DPAT for 5-HT$_{1A}$ receptors. The reversal of agonist induced inhibition of forskolin-stimulated adenylate cyclase activity is calculated in relation to the 32 nM agonist effect.

The following Examples are provided solely for the purposes of illustration and do not limit the invention which is defined by the claims.

EXAMPLE 1

(7RS,8aSR)-7-(4-Fluorophenoxy)methyl-2-(5-fluoropyrimidin-2-yl)-1,2,3,4,6,7,8,8a-octahydro-pyrrolo[1,2-a]pyrazine

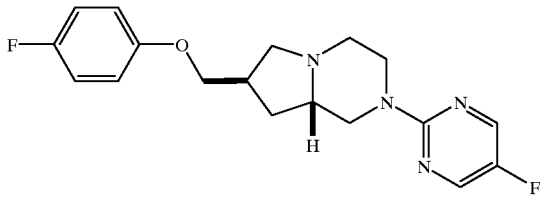

A solution of 2.00 g (5.9 mmol) of (7RS,8aSR)-7-(4-fluorophenoxy)methyl-2-phenylmethyl-1,2,3,4,6,7,8,8a-octahydro-pyrrolo[1,2-a]pyrazine (Preparation 2) and 4.1 mL (20.6 mmol) of 5M aqueous ammonium formate in 50 mL methanol was treated with an aqueous slurry of 0.200 g of 10% Pd/C. The reaction was refluxed for 48 hours. The mixture was filtered and the solvent removed in vacuo to give an oily residue. The crude (7RS,8aSR)-7-(4-fluorophenoxy)methyl-1,2,3,4,6,7,8,8a-octahydro-pyrrolo[1,2-a]pyrazine was combined with 1.2 g (9.1 mmol) of 2-chloro-5-fluoropyrimidine (Dunaiskis, A. et al., *Org. Prep. Proc. Int.*, 1995, 27, 600–602), 2.0 g (9.1 mmol) of sodium carbonate in 100 mL of water, and the mixture was gently refluxed for 16 hours. After cooling to room temperature, the mixture was extracted with methylene chloride (3×). The combined organic layers were dried (magnesium sulfate), filtered, and evaporated. Purification by flash silica gel chromatography eluting with 90:10 ethyl acetate:hexane gave 0.744 g (27%) of the title compound. Mp (.HCl) 120–122° C. $^3$C NMR (base, CDCl$_3$): δ 31.4, 35.3, 43.8, 49.0, 51.5, 57.6, 61.5, 71.4, 115.39, 115.50, 115.62, 115.92, 144.96, 145.24, 149.9, 153.2, 155.1, 155.7, 158.8. Anal. calc'd for C$_{18}$H$_{20}$F$_2$N$_4$O: C, 62.41; H, 5.82; N, 16.18. Found: C, 62.05, H, 5.99; N, 16.33.

EXAMPLE 2

(7SR,8aSR)-7-(4-Fluorophenoxy)methyl-2-(5-fluoropyrimidin-2-yl)-1,2,3,4,6,7,8,8a-octahydro-pyrrolo[1,2-a]pyrazine

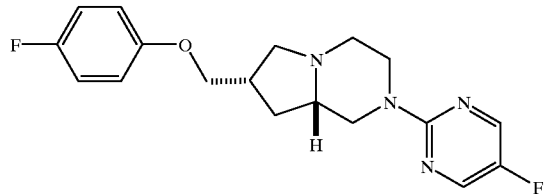

A solution of 0.870 g (2.6 mmol) of (7SR,8aSR)-7-(4-fluorophenoxy)methyl-2-phenylmethyl-1,2,3,4,6,7,8,8a-octahydro-pyrrolo[1,2-a]pyrazine (Preparation 2) and 1.8 mL (8.9 mmol) of 5M aqueous ammonium formate in 50 mL methanol was treated with an aqueous slurry of 0.100 g of 10% Pd/C. The reaction was refluxed for 24 hours. The mixture was filtered and the solvent removed in vacuo to give an oily residue. The crude (7SR,8aSR)-7-(4-fluorophenoxy)methyl-1,2,3,4,6,7, 8,8a-octahydro-pyrrolo[1,2-a]pyrazine was combined with 0.373 g (2.8 mmol) of 2-chloro-5-fluoropyrimidine (Dunaiskis, A. et al., *Org. Prep. Proc. Int.*, 1995, 27, 600–602), 0.650 g (6.1 mmol) of sodium carbonate in 50 mL of water, and the mixture was gently refluxed for 16 hours. After cooling to room temperature, the mixture was extracted with methylene chloride (3×). The combined organic layers were dried (magnesium sulfate), filtered, and evaporated. Purification by silica gel flash chromatography eluting with 85:15 ethyl acetate:hexane gave 0.444 g (50%) of the title compound. Mp (.HCl) 211–213° C. $^{13}$C NMR (base, CDCl$_3$): δ 31.7, 35.2, 43.8, 49.1, 51.4, 56.6, 62.3, 72.5, 115.45, 115.56, 115.89, 144.95, 145.24, 149.9, 153.2, 155.1, 155.6, 158.79, 158.90. Anal. calc'd for C$_{18}$H$_{20}$F$_2$N$_4$O: C, 62.41; H, 5.82; N, 16.18. Found: C, 62.15, H, 5.99; N, 16.38.

EXAMPLE 3

(7RS,8aSR)-7-(4-Fluorophenoxy)methyl-2-(5-fluoropyrimidin-2-yl)-7-methyl-1,2,3,4,6,7,8,8a-octahydro-pyrrolo[1,2-a]pyrazine

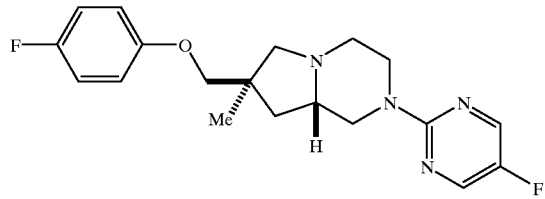

A solution of 0.745 g (2.80 mmol) of (7RS,8aSR)-7-hydroxymethyl-2-(5-fluoropyrimidin-2-yl)-7-methyl-1,2,3,4,6,7,8,8a-octahydro-pyrrolo[1,2-a]pyrazine (Preparation 5) and 0.43 mL (3.08 mmol) of triethylamine in 30 mL of dry methylene chloride was chilled to 0° C., and treated with methanesulfonyl chloride (0.228 mL, 2.94 mmol) in 15 mL of dry methylene chloride. After 1 hour, the solution was washed with water (2×), dried (magnesium sulfate), filtered and evaporated to give 0.915 g (95%) of mesylate as a pale yellow solid.

A solution of 0.23 g (2.0 mmol) of 4-fluorophenol in 10 mL of dry DMF was treated with 0.096 g (2.4 mmol) of sodium hydride (60% oil dispersion), and the mixture heated at 50° C. for 1 hour. A solution of 0.25 g (0.73 mmol) of mesylate in 10 mL of dry DMF was added and the solution heated at 100° C. for 72 hours. The mixture was cooled to room temperature, diluted with water, and extracted with diethyl ether (2×). The organic phase was dried (magnesium sulfate), filtered and evaporated. Purification by flash silica gel chromatography eluting with 2:1 petroleum ether:diethyl ether gave 0.15 g (58%) of the title compound. Mp (.HCl) 158–160° C. $^{13}$C NMR (base, CDCl$_3$): δ 26.4, 39.9, 40.6, 43.8, 49.1, 51.6, 62.8, 64.5, 76.0, 115.3, 115.5, 115.6, 115.9, 145.0, 145.2, 149.9, 153.2, 155.4, 155.7, 158.8, 158.9. HRMS calc'd for C$_{19}$H$_{23}$F$_2$N$_4$O (MH+): 361.1840; found: 361.1861.

EXAMPLE 4

(7RS,8aSR)-7-Phenoxymethyl-2-(5-fluoropyrimidin-2-yl)-7-methyl-1,2,3,4,6,7,8,8a-octahydro-pyrrolo[1,2-a]pyrazine

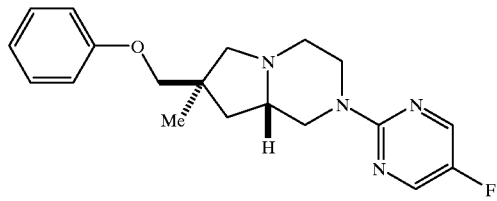

A solution of 0.745 g (2.80 mmol) of (7RS,8aSR)-7-hydroxymethyl-2-(5-fluoropyrimidin-2-yl)-7-methyl-1,2,3,4,6,7,8,8a-octahydro-pyrrolo[1,2-a]pyrazine (Preparation 5) and 0.43 mL (3.08 mmol) of triethylamine in 30 mL of dry methylene chloride was chilled to 0° C., and treated with methanesulfonyl chloride (0.228 mL, 2.94 mmol) in 15 mL of dry methylene chloride. After 1 hour, the solution was washed with water (2×), dried (magnesium sulfate), filtered and evaporated to give 0.915 g (95%) of mesylate as a pale yellow solid.

A solution of 0.19 g (2.0 mmol) of phenol in 10 mL of dry DMF was treated with 0.096 g (2.4 mmol) of sodium hydride (60% oil dispersion), and the mixture heated at 50° C. for 1 hour A solution of 0.25 g (0.73 mmol) of mesylate in 10 mL of dry DMF was added and the solution heated at 100° C. for 72 hours. The mixture was cooled to room temperature, diluted with water, and extracted with diethyl ether (2×). The organic phase was dried (magnesium sulfate), filtered and evaporated. Purification by flash silica gel chromatography eluting with petroleum ether:diethyl ether (2:1) gave 0.18 g (72%) of the title compound. Mp (.HCl) 189–191° C. $^{13}$C NMR (base, CDCl$_3$): δ 26.4, 40.0, 40.6, 43.8, 49.1, 51.6, 62.8, 64.5, 75.3, 114.5, 120.7, 129.4, 145.0, 145.2, 149.9, 153.2, 158.9, 159.3. HRMS calc'd for C$_{19}$H$_{23}$FN$_4$O (MH+): 343.1934; found: 343.1951.

EXAMPLE 5

(7RS,8aSR)-7-(4-Fluorophenoxy)methyl-2-(5-chloropyridin-2-yl)-1,2,3,4,6,7,8,8a-octahydro-pyrrolo[1,2-a]pyrazine

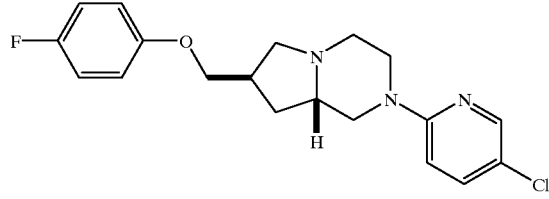

A mixture of 3.8 g (26 mmol) of 2,5-dichloropyridine, 1.3 g (12 mmol) of sodium carbonate, 1.3 g (5.2 mmol) of (7RS,8aSR)-7-(4-fluorophenoxy)methyl-1,2,3,4,6,7,8,8a-octahydro-pyrrolo[1,2-a]pyrazine (Preparation 2), and 20 mL of isoamyl alcohol was heated at reflux for 18 hours. The solvent was evaporated, the residue taken up in water and ethyl acetate, and the pH adjusted to 11 with sodium carbonate. The layers were separated and the organic phase was dried (magnesium sulfate), filtered, and evaporated. Purification by medium pressure silica gel chromatography with ethyl acetate gave 35 mg (2%) of the title compound. Mp (.HCl) 202–206° C. HRMS calc'd for C$_{19}$H$_{21}$ClFN$_3$O (MH+): 362.1435, found: 362.1451.

EXAMPLE 6

(7S,8aS)-7-(4-Fluorophenoxy)-2-(5-fluoropyrimidin-2-yl)-1,2,3,4,6,7,8,8a-octahydro-pyrrolo[1,2-a] pyrazine

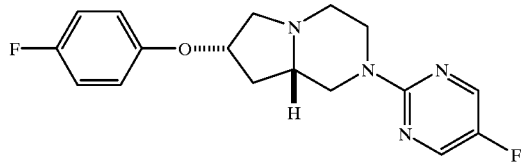

A solution of 0.971 g (4.18 mmol) of (7R,8aS)-7-hydroxy-2-phenylmethyl-1,2,3,4,6,7,8,8a-octahydro-pyrrolo[1,2-a]pyrazine (Diafi, L. et al., *J. Het. Chem.*, 1990, 27, 2181), 0.703 g (6.27 mmol) of 4-fluorophenol and 1.32 g (5.02 mmol) of triphenylphosphine in 20 mL of dry THF was treated with 0.79 mL (5.02 mmol) of diethyl azodicarboxylate and the solution stirred at room temperature for 21 hours. Excess HCl (g) in diethyl ether was added, the precipitate was collected on a Buchner funnel, washing with ethyl acetate. The gummy residue was dissolved in a mixture of ethyl acetate and aqueous ammonium hydroxide, the layers were separated, the aqueous phase was extracted with more ethyl acetate (2×), the combined organic phase was dried (magnesium sulfate), filtered and evaporated. Purification by silica gel MPLC with 95:5 ethyl acetate:methanol gave 1.3 g (95%) of (7S,8aS)-7-(4-fluorophenoxy)-2-phenylmethyl-1,2,3,4,6,7,8,8a-octahydro-pyrrolo[1,2-a]pyrazine.

A solution of 0.83 g (2.5 mmol) of (7S,8aS)-7-(4-fluorophenoxy)-2-phenylmethyl-1,2,3,4,6,7,8,8a-octahydro-pyrrolo[1,2-a]pyrazine in 10 mL of methanol and 1.8 mL of aqueous ammonium formate (5 M) was treated with an aqueous slurry of 0.325 g of 10% palladium on carbon and the mixture was stirred at room temperature for 24 hours. The mixture was filtered through Celite, evaporated, re-evaporated with another 100 mL of chloroform, dissolved in 100 mL of chloroform, dried (magnesium sulfate), filtered and evaporated. The crude amine (0.61 g, ca. 2.5 mmol), 0.50 g (3.75 mmol) of 2-chloro-5-fluoropyrimidine (Dunaiskis, A. et al., Org. Prep. Proc. Int., 1995, 27, 600–602), 0.86 g (6.2 mmol) of potassium carbonate and 15 mL of 2-propanol were refluxed for 5.5 hours. The mixture was cooled to room temperature, diluted with water, and extracted with ethyl acetate (3×). The combined organic phase was washed with water (2×) and brine (1×), dried (magnesium sulfate), filtered and evaporated. Purification by silica gel MPLC starting with 70:30 ethyl acetate:hexane and ramping to 50:50 ethyl acetate: hexane at 30 minutes, gave 0.30 g (36%) of the title compound. Mp (.HCl) 90–95° C. $^{13}$C NMR (base, CDCl$_3$): δ 36.6, 43.6, 48.7, 60.5, 62.1, 75.6, 115.67, 115.98, 116.08, 116.18, 144.97, 145.26, 149.9, 153.2, 153.8, 155.6, 158.8. HRMS calc'd for $C_{17}H_{19}F_2N_4O$ (MH+): 333.1527, found: 333.1556.

EXAMPLE 7

(7R,8aS)-7-(4-Fluorobenzyl)oxy-2-(5-fluoropyrimidin-2-yl)-1,2,3,4,6,7,8,8a-octahydro-pyrrolo[1,2-a]pyrazine

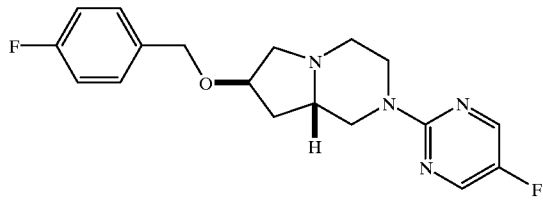

A solution of 0.75 g (3.15 mmol) of (7R,8aS)-7-hydroxy-2-(5-fluoropyrimidin-2-yl)-1,2,3,4,6,7,8,8a-octahydro-pyrrolo[1,2-a]pyrazine (Preparation 6) and 0.79 mL (6.3 mmol) of 4-fluorobenzyl bromide in 30 mL of dry DMF was treated with 0.15 g (3.8 mmol) of sodium hydride (60% oil dispersion), and the mixture was heated at 100° C. for 18 hours. The mixture was cool, diluted with water, and extracted with diethyl ether (5×). The combined organic phase was dried (magnesium sulfate), filtered and evaporated. Purification by flash silica gel chromatograph with 50:50 ethyl acetate:hexane gave 0.090 g (8%) of the title compound. Mp (.HCl) 74–79° C. $^{13}$C NMR (base, CDCl$_3$): δ 35.6, 43.9, 48.9, 51.2, 60.4, 60.7, 70.7, 76.7, 115.1, 115.4, 129.35, 129.46, 133.9, 144.9, 145.2, 149.9, 153.2, 158.9, 164.0. HRMS calc'd for $C_{18}H_{20}F_2N_4O$ (MH+): 347.1683, found: 347.1671.

EXAMPLE 8

(7S,8aS)-7-(4-Fluorobenzyl)oxy-2-(5-fluoropyrimidin-2-yl)-1,2,3,4,6,7,8,8a-octahydro-pyrrolo[1,2-a]pyrazine

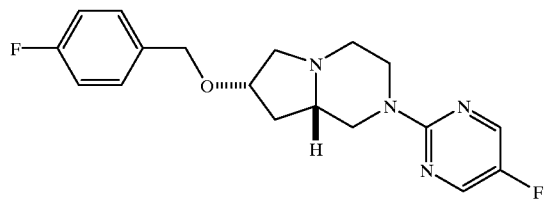

A solution of 1.15 mL (10.2 mmol) of 4-fluorobenzyl alcohol in 35 mL of dry DMF was treated with 0.48 g (12 mmol) of sodium hydride (60% oil dispersion), and the mixture was stirred at 50° C. for 30 minutes. A solution of 1.15 g (3.64 mmol) of (7R,8aS)-7-methanesulfonyloxy-2-(5-fluoropyrimidin-2-yl)-1,2,3,4,6,7,8,8a-octahydro-pyrrolo[1,2-a]pyrazine (Preparation 7) in 35 mL of dry DMF was added and the solution stirred at 100° C. for 18 hours. The solution was cooled, diluted with water, and extracted with diethyl ether (2×). The combined organic phase was dried (magnesium sulfate), filtered and evaporated. Purification by flash silica gel chromatography with ethyl acetate gave 0.25 g (20%) of the title compound. Mp (.D-(−)-tartrate) 76–81° C. $^{13}$C NMR (base, CDCl$_3$): δ 36.3, 43.6, 48.8, 51.3, 60.2, 61.9, 70.4, 76.6, 115.0, 115.3, 129.43, 129.53, 134.0, 144.9, 145.2, 149.9, 153.2, 158.9, 160.6, 163.9. HRMS calc'd for $C_{18}H_{20}F_2N_4O$ (MH+): 347.1683, found: 347.1706.

EXAMPLE 9

(7S,8aS)-2-(5-Fluoropyrimidin-2-yl)-1,2,3,4,6,7,8,8a-octahydro-pyrrolo[1,2-a]pyrazin-7-yl benzoate

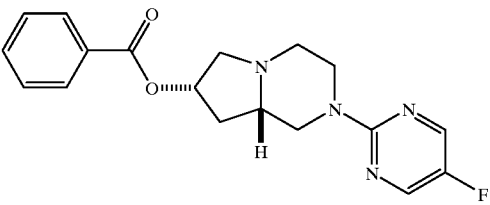

A solution of 2.0 g (8.4 mmol) of (7R,8aS)-7-hydroxy-2-(5-fluoropyrimidin-2-yl)-1,2,3,4,6,7,8,8a-octahydro-pyrrolo[1,2-a]pyrazine (Preparation 6), 1.54 g (12.6 mmol) of benzoic acid, 2.65 g(10.1 mmol) of triphenylphosphine, and 1.59 mL (10.1 mmol) of diethyl azodicarboxylate (DEAD) in 85 mL of THF was stirred at ambient temperature for 16 hours. The solvent was evaporated, and flash silica gel chromatography with 1:1 hexane:ethyl acetate gave 2.5 g of partially purified material. A second chromatography with 10:1 methylene chloride:methanol gave 1.68 g (59%) of the title compound. Mp (.HCl) 134–135.5° C. $^{13}$C NMR (base, CDCl$_3$): δ 36.1, 43.7, 48.7, 51.2, 60.4, 61.8, 73.2, 128.3, 129.7, 130.1, 133.0, 145.0, 145.3, 150.0, 153.1, 158.9, 166.7. HRMS calc'd for $C_{18}H_{20}FN_4O$ (MH+): 343.1570, found: 343.1585.

EXAMPLE 10

(7S,8aS)-7-(4-Fluorophenoxy)methyl-2-(5-fluoropyrimidin-2-yl)-1,2,3,4,6,7,8,8a-octahydro-pyrrolo[1,2-a]pyrazine

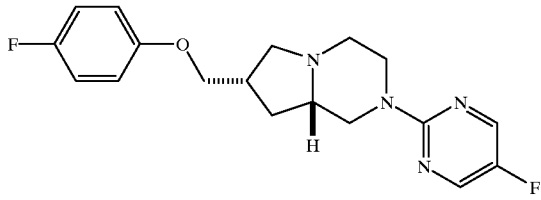

A solution of 0.25 g (0.99 mmol) of (7S,8aS)-7-hydroxymethyl-2-(5-fluoropyrimidin-2-yl)-1,2,3,4,6,7,8,8a-octahydro-pyrrolo[1,2-a]pyrazine (Preparation 13), 0.167 g (1.49 mmol) of 4-fluorophenol, 0.31 g (1.19 mmol) of triphenylphosphine and 0.19 mL (1.2 mmol) of diethyl azodicarboxylate (DEAD) in 10 mL of dry THF was stirred at ambient temperature for 16 hours. The solvent was evaporated, the residue was dissolved in chloroform and washed with 1M sodium hydroxide. The organic phase was dried (magnesium sulfate), filtered and evaporated. Purification by flash silica gel chromatography with 1:1 hexane:ethyl acetate and a second chromatography with 3:1 hexane:ethyl acetate gave 0.185 g (54%) of the title compound. Mp (.HCl) 207.5–208° C. $^{13}$C NMR (base, CDCl$_3$): δ 31.7, 35.2, 43.8, 49.1, 51.4, 56.6, 62.3, 72.5, 115.5, 115.6, 115.9, 144.9, 145.2, 149.9, 153.2, 155.1, 155.6, 158.8, 158.9. m/z (MH+) 347.

EXAMPLE 11

(7S,8aS)-7-(Substituted-phenoxy)methyl-2-(5-fluoropyrimidin-2-yl)-1,2,3,4,6,7,8,8a-octahydro-pyrrolo[1,2-a]pyrazines

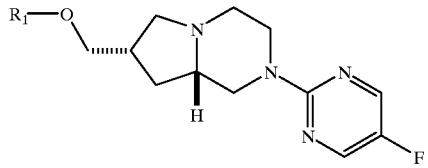

The following compounds were prepared from (7S,8aS)-7-hydroxymethyl-2-(5-fluoropyrimidin-2-yl)-1,2,3,4,6,7,8,8a-octahydro-pyrrolo[1,2-a]pyrazine (Preparation 13) and the appropriate phenol according to the method described in Example 10.

11a. 7S,8aS)-7-(3-Cyanophenoxy)methyl-2-(5-fluoropyrimidin-2-yl)-1,2,3,4,6,7,8,8a-octahydro-pyrrolo[1,2-a]pyrazine: Mp (.HCl) 83–85° C. HRMS calc'd for C$_{19}$H$_{21}$FN$_5$O (MH+): 354.1730, found: 354.1716.

11b. 7S, 8aS)-7-(4-Cyanophenoxy)methyl-2-(5-fluoropyrimidin-2-yl)-1,2,3,4,6,7,8,8a-octahydro-pyrrolo[1,2-a]pyrazine: Mp (.HCl) 183–185° C. HRMS calc'd for C$_{19}$H$_{21}$FN$_5$O (MH+):354.1730, found: 354.1719.

11c. (7S,8aS)-7-(3,5-Difluorophenoxy)methyl-2-(5-fluoropyrimidin-2-yl)-1,2,3,4,6,7,8,8a-octahydro-pyrrolo[1,2-a]pyrazine: Mp (.HCl) 205–206° C. HRMS calc'd for C$_{18}$H$_{20}$F3N$_4$O (MH+): 365.1589, found: 365.1592.

11d. (7S,8aS)-7-(2-Nitrophenoxy)methyl-2-(5-fluoropyrimidin-2-yl)-1,2,3,4,6,7,8,8a-octahydro-pyrrolo[1,2-a]pyrazine: Mp (.HCl) 151–153° C. H C$_{18}$H$_{21}$FN$_5$O$_3$ (MH+): 374.1628, found: 374.1638.

11e. (7S,8aS)-7-(3-Nitrophenoxy)methyl-2-(5-fluoropyrimidin-2-yl)-1,2,3,4,6,7,8,8a-octahydro-pyrrolo[1,2-a]pyrazine: Mp (.HCl) 92–9° C. HRMS calc'd for C$_{18}$H$_{21}$FN$_5$O$_3$ (MH+): 374.1628, found: 374.1647.

11f. (7S,8aS)-7-(4-Nitrophenoxy)methyl-2-(5-fluoropyrimidin-2-yl)-1,2,3,4,6,7,8,8a-octahydro-pyrrolo[1,2-a]pyrazine: Mp (.HCl) 189–191° C. HRMS calc'd for C$_{18}$H$_{21}$FN$_5$O$_3$(MH+): 374.1628, found: 374.1647.

11 g. (7S,8aS)-7-(3-(Trifluoromethyl)phenoxy)methyl-2-(5-fluoropyrimidin-2-yl)-1,2,3,4,6,7,8,8a-octahydro-pyrrolo[1,2-a]pyrazine: HRMS calc'd for C$_{19}$H$_{21}$F$_4$N$_4$O (MH+): 397.1651, found: 397.1642.

11h. (7S,8aS)-7-(4-(Cyanomethyl)phenoxy)methyl-2-(5-fluoropyrimidin-2-yl)-1,2,3,4,6,7,8,8a-octahydro-pyrrolo[1,2-a]pyrazine: Mp (.HCl) 65–67° C. HRMS calc'd for C$_{20}$H$_{23}$FN$_5$O (MH+): 368.1887, found: 368.1898.

11I. (7S,8aS)-7-(4-((Methoxycarbonyl)methyl)phenoxy)methyl-2-(5-fluoropyrimidin-2-yl)-1,2,3,4,6,7,8,8a-octahydro-pyrrolo[1,2-a]pyrazine: Mp (.HCl) 50–52° C. HRMS caic'd for C$_{21}$H$_{25}$FN$_4$O$_3$ (MH+): 401.1989, found: 401.1965.

11j. (7S,8aS)-7-(3-(Methoxycarbonyl)phenoxy)methyl-2-(5-fluoropyrimidin-2-yl)-1,2,3,4,6,7,8,8a-octahydro-pyrrolo[1,2-a]pyrazine: Mp (.HCl) 74–79° C. HRMS calc'd for C$_{20}$H$_{24}$FN$_4$O$_3$ (MH+): 387.1832, found: 387.1866.

11k. (7S,8aS)-7-(3-(Ethynyl)phenoxy)methyl-2-(5-fluoropyrimidin-2-yl)-1,2,3,4,6,7,8,8a-octahydro-pyrrolo[1,2-a]pyrazine: Mp (.HCl) 73–76° C. HRMS calc'd for C$_{20}$H$_{22}$FN$_4$O (MH+): 353.1778, found: 353.1805.

11l. (7S,8aS)-7-(3-(Ethoxy)phenoxy)methyl-2-(5-fluoropyrimidin-2-yl)-1,2,3,4,6,7,8,8a-octahydro-pyrrolo[1,2-a]pyrazine: Mp (.HCl) 169–17° C. HRMS calc'd for C$_{20}$H$_{26}$FN$_4$O$_2$ (MH+): 373.2040, found: 373.2016.

11m. (7S,8aS)-7-(Phenoxy)methyl-2-(5-fluoropyrimidin-2-yl)-1,2,3,4,6,7,8,8a-octahydro-pyrrolo[1,2-a]pyrazine: Mp (.HCl) 76–79° C. HRMS calc'd for C$_{18}$H$_{22}$FN$_4$O (MH+): 329.1778, found: 329.1784.

EXAMPLE 12

(7S,8aS)-7-(4-Fluorophenoxy)methyl-2-(5-chloropyridin-2-yl)-1,2,3,4,6,7,8,8a-octahydro-pyrrolo[1,2-a]pyrazine

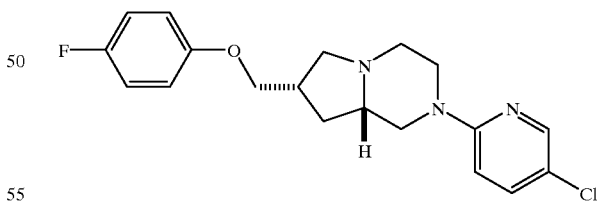

A solution of 0.25 g (0.93 mmol) of (7S,8aS)-7-hydroxymethyl-2-(5-chloropyridin-2-yl)-1,2,3,4,6,7,8,8a-octahydro-pyrrolo[1,2-a]pyrazine (Preparation 14), 0.157 g (1.40 mmol) of 4-fluorophenol, 0.29 g (1.12 mmol) of triphenylphosphine and 0.18 mL (1.1 mmol) of diethyl azodicarboxylate (DEAD) in 10 mL of dry THF was stirred at ambient temperature for 16 hours. The solvent was evaporated, the residue was dissolved in chloroform and washed with 1M sodium hydroxide. The organic phase was dried (magnesium sulfate), filtered and evaporated. Purification by flash silica gel chromatography with 1:1 hexane:ethyl acetate gave 0.24 g (71%) of the title compound. Mp (.HCl) 221–224° C. HRMS calc'd for $C_{19}H_{22}ClFN_3O$ (MH+): 362.1435, found: 362.1415.

EXAMPLE 13

(7S,8aS)-7-(Substituted-phenoxy)methyl-2-(5-chloropyridin-2-yl)-1,2,3,4,6,7,8,8a-octahydro-pyrrolo[1,2-a]pyrazines

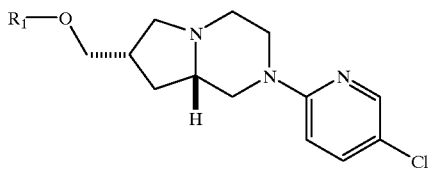

The following compounds were prepared from (7S,8aS)-7-hydroxymethyl-2-(5-chloropyridin-2-yl)-1,2,3,4,6,7,8,8a-octahydro-pyrrolo[1,2-a]pyrazine (Preparation 14) and the appropriate phenol according to the method described in Example 12.

13a. (7S,8aS)-7-(3-Cyanophenoxy)methyl-2-(5-chloropyridin-2-yl)-1,2,3,4,6,7,8,8a-octahydro-pyrrolo[1,2-a]pyrazine: Mp (.HCl) 220–224° C. HRMS calc'd for $C_{20}H_{22}ClN_4O$ (MH+): 369.1482, found: 369.1472.

13b. (7S,8aS)-7-(4-Cyanophenoxy)methyl-2-(5-chloropyridin-2-yl)-1,2,3,4,6,7,8,8a-octahydro-pyrrolo[1,2-a]pyrazine. Purification by flash silica gel chromatography with ethyl ether. Mp (.HCl) 245° C. (dec). HRMS calc'd for $C_{20}H_{22}ClN_4O$ (MH+): 369.1482, found: 369.1465.

13c. (7S,8aS)-7-(3,5-Difluorophenoxy)methyl-2-(5-chloropyridin-2-yl)-1,2,3,4,6,7,8,8a-octahydro-pyrrolo[1,2-a]pyrazine. Purification by flash silica gel chromatography with 65:35 diethyl ether:petroleum ether. Mp (.HCl) 220° C. (dec). HRMS calc'd for $C_{19}H_{21}ClF_2N_3O$ (MH+): 380.1341, found: 380.1309.

13d. (7S,8aS)-7-(4-(Methoxycarbonyl)methylphenoxy)methyl-2-(5-chloropyridin-2-yl)-1,2,3,4,6,7,8,8a-octahydro-pyrrolo[1,2-a]pyrazine: Mp (.HCl) 186–189° C. HRMS calc'd for $C_{22}H_{27}ClN_3O_3$ (MH+): 416.1741, found: 416.1765.

EXAMPLE 14

(7S,8aS)-7-(3-Cyanophenoxy)methyl-2-(5-cyanopyridin-2-yl)-1,2,3,4,6,7,8,8a-octahydro-pyrrolo[1,2-a]pyrazine

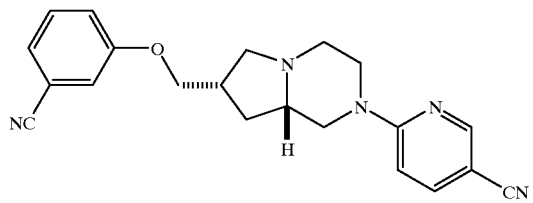

A solution of 1.0 g (6.4 mmol) of (7S,8aS)-7-hydroxymethyl-1,2,3,4,6,7,8,8a-octahydro-pyrrolo[1,2-a]pyrazine (Preparation 13, Step A), 1.77 g (12.8 mmol) of 2-chloro-5-cyanopyridine and 2.71 g (25.6 mmol) of sodium carbonate in 50 mL of isoamyl alcohol was heated at reflux for 18 hours. The mixture was cooled to room temperature, diluted with ethyl acetate and water, the pH was adjusted to 11 with sodium carbonate, the layers were separated, and the aqueous layer extracted with ethyl acetate. The combined organic phase was dried (magnesium sulfate), filtered and evaporated to give (7S,8aS)-7-hydroxymethyl-2-(5-cyanopyridin-2-yl)-1,2,3,4,6,7,8,8a-octahydro-pyrrolo[1,2-a]pyrazine.

The (7S,8aS)-7-hydroxymethyl-2-(5-cyanopyridin-2-yl)-1,2,3,4,6,7,8,8a-octahydro-pyrrolo[1,2-a]pyrazine, 1.6 g (13.4 mmol) of 3-cyanophenol, and 2.8 g (11 mmol) of triphenylphosphine were dissolved in 20 mL of dry THF, the solution was treated with 1.7 mL (11 mmol) of diethyl azodicarboxylate (DEAD), and the reaction stirred at ambient temperature for 16 hours. The solvent was evaporated, the residue taken up in ethyl acetate, and washed with 1M NaOH (sodium hydroxide). The organic phase was extracted with 1M HCl (3×), and the aqueous acid was washed with ethyl acetate (1×). The aqueous phase was made basic with 1M NaOH, extracted with ethyl acetate (3×), and the combined organic phase dried (magnesium sulfate), filtered and evaporated. Purification by flash silica gel chromatography with 75:25 ethyl acetate:hexane gave 0.603 g (19%) of the title compound. Mp (.HCl) 197–200° C. HRMS calc'd for $C_{21}H_{22}N_5O$ (MH+): 360.1824, found: 360.1802.

EXAMPLE 15

(7S,8aS)-7-(4-Fluorophenoxy)methyl-2-(4-cyanophenyl)-1,2,3,4,6,7,8,8a-octahydro-pyrrolo[1,2-a]pyrazine

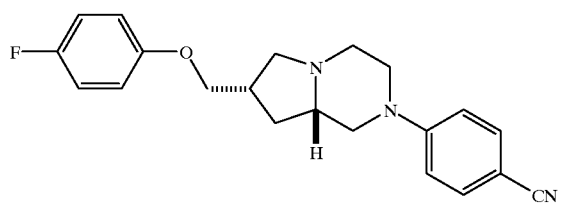

A solution of 0.25 g (0.97 mmol) of (7S,8aS)-7-hydroxymethyl-2-(4-cyanophenyl)-1,2,3,4,6,7,8,8a-octahydro-pyrrolo[1,2-a]pyrazine (Preparation 16), 0.164 g (1.46 mmol) of 4-fluorophenol, 0.31 g (1.15 mmol) of triphenylphosphine in 10 mL of THF was treated with 0.18 mL (1.15 mmol) of diethyl azodicarboxylate and the solution stirred at ambient temperature for 16 hours. The solvent was removed by rotary evaporation, and the residue partitioned between chloroform and 1M sodium hydroxide. The layers were separated, and the organic phase was dried (magnesium sulfate), filtered and evaporated. Purification by flash silica gel chromatography with 1:1 ethyl acetate:hexane gave 0.225 g (66%) of the title compound. Mp (.HCl) 81–85° C. HRMS calc'd for $C_{21}H_{23}FN_3O$ (MH+): 352.1825, found: 352.1817.

EXAMPLE 16

(7S,8aS)-7-(Substituted-phenoxy)methyl-2-(4-cyanophenyl)-1,2,3,4,6,7,8,8a-octahydro-pyrrolo[1,2-a]pyrazine

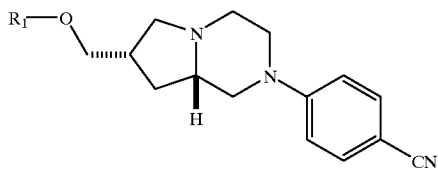

The following compounds were prepared from (7S,8aS)-7-hydroxymethyl-2-(4-cyanophenyl)-1,2,3,4,6,7,8,8a-octahydro-pyrrolo[1,2-a]pyrazine (Preparation 16) and the appropriate phenol according to the method described in Example 15.

16a. (7S,8aS)-7-(3-Cyanophenoxy)methyl-2-(4-cyanophenyl)-1,2,3,4,6,7,8,8a-octahydro-pyrrolo[1,2-a]pyrazine. Mp 114–118° C. HRMS calc'd for $C_{22}H_{23}N_4O$ (MH+): 359.1872, found: 359.1877.

16b. (7S,8aS)-7-(4-Cyanophenoxy)methyl-2-(4-cyanophenyl)-1,2,3,4,6,7,8,8a-octahydro-pyrrolo[1,2-a]pyrazine. Mp 128–135° C. HRMS calc'd for $C_{22}H_{23}N_4O$ (MH+): 359.1872, found: 359.1879.

16c. (7S,8aS)-7-(3-Ethoxyphenoxy)methyl-2-(4-cyanophenyl)-1,2,3,4,6,7,8,8a-octahydro-pyrrolo[1,2-a]pyrazine. Mp 94–98° C. HRMS calc'd for $C_{23}H_{28}N_3O_2$ (MH+): 378.2182, found: 378.2145.

EXAMPLE 17

(7S,8aS)-2-(5-Chloropyridin-2-yl)-1,2,3,4,6,7,8,8a-octahydro-pyrrolo[1,2-a]pyrazin-7-ylbenzoate

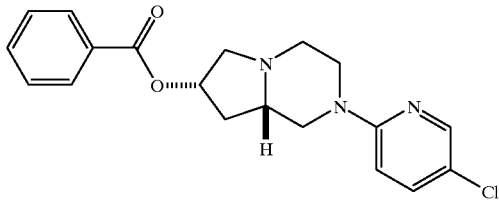

A solution of 0.595 g (2.35 mmol) of (7R,8aS)-7-hydroxy-2-(5-chloropyridin-2-yl)-1,2,3,4,6,7,8,8a-octahydro-pyrrolo[1,2-a]pyrazine (Preparation 17), 0.430 g (3.52 mmol) of benzoic acid and 0.738 g (2.81 mmol) of triphenylphosphine in 25 mL of dry THF was treated with 0.44 mL (2.8 mmol) of diethyl azodicarboxylate, and the mixture stirred at ambient temperature for 16 hours. The solvent was evaporated and the residue purified by flash silica gel chromatography with 10:1 methylene chloride:acetone. A second chromatography of the major fraction with the same system gave 0.63 g (75%) of the title compound. Mp (.HCl) 202–205° C. HRMS calc'd for $C_{19}H_{21}ClN_3O_2$ (MH+): 358.1322, found: 358.1320.

EXAMPLE 18

(7S,8aS)-7-(4-Fluorobenzyl)oxy-2-(5-chloropyridin-2-yl)-1,2,3,4,6,7,8,8a-octahydro-pyrrolo[1,2-a]pyrazine

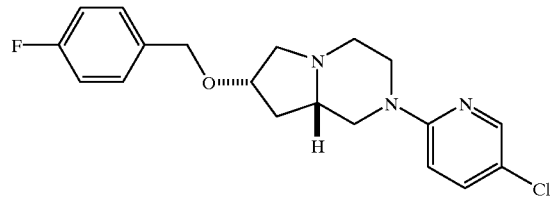

A solution of 0.23 g (0.91 mmol) of (7S,8aS)-7-hydroxy-2-(5-chloropyridin-2-yl)-1,2,3,4,6,7,8,8a-octahydro-pyrrolo[1,2-a]pyrazine (Preparation 18) in 10 mL of dry THF was treated with 40 mg (1.0 mmol) of sodium hydride (60% oil dispersion), followed by 0.125 mL (1.0 mmol) of 4-fluorobenzyl bromide and 17 mg (0.05 mmol) of tetra-n-butylammonium iodide. The mixture was stirred at ambient temperature for 16 hours, and warmed to 50° C. for 4 hours. The suspension was cooled, the solvent was evaporated, and the residue partitioned between ethyl acetate and water. The layers were separated, and the organic phase was dried (magnesium sulfate), filtered and evaporated. Purification by flash silica gel chromatography with 95:5 chloroform:methanol gave 0.135 g (41%) of the title compound. Mp (.HCl) 165–168° C. HRMS calc'd for $C_{19}H_{22}ClFN_3O$ (MH+): 362.1435, found: 362.1451.

EXAMPLE 19

(7S,8aS)-7-(3-Cyanobenzyl)oxy-2-(5-fluoropyrimidin-2-yl)-1,2,3,4,6,7,8,8a-octahydro-pyrrolo[1,2-a]pyrazine

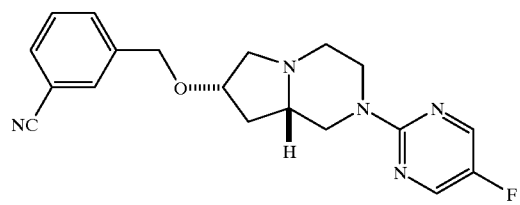

A solution of 0.60 g (2.5 mmol) of (7S,8aS)-7-hydroxy-2-(5-fluoropyrimidin-2-yl)-1,2,3,4,6,7,8,8a-octahydro-pyrrolo[1,2-a]pyrazine (Preparation 15) in 30 mL of THF was treated with 0.41 g (10 mmol) of sodium hydride (60% oil dispersion), followed by 0.75 g (3.8 mmol) of 3-cyanobenzyl bromide and 30 mg (0.1 mmol) of tetra-n-butylammonium iodide. The mixture was stirred 50° C. for 16 hours, cooled to room temperature, the solvent was evaporated, and the residue partitioned between ethyl acetate and water. The layers were separated, the organic phase was washed with water and brine, dried (magnesium sulfate), filtered and evaporated. Purification by MPLC silica gel chromatography with ethyl acetate gave 0.11 g (12%) of the title compound. Mp (.HCl) 95–100° C. HRMS calc'd for $C_{19}H_{21}FN_5O$ (MH+): 345.1730; found: 345.1739.

EXAMPLE 20

(7S,8aS)-7-(4-(2-Hydroxyethyl)phenoxy)methyl-2-(5-fluoropyrimidin-2-yl)-1,2,3,4,6,7,8,8a-octahydro-pyrrolo[1,2-a]pyrazine

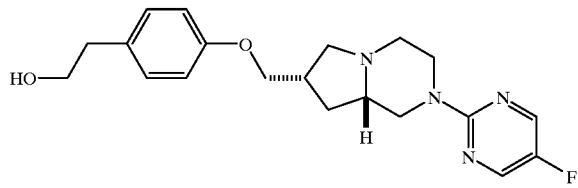

A solution of 0.13 g (0.33 mmol) of (7S,8aS)-7-(4-((methoxycarbonyl)methyl)phenoxy)methyl-2-(5-fluoropyrimidin-2-yl)-1,2,3,4,6,7,8,8a-octahydro-pyrrolo[1,2-a]pyrazine (Example 11i) in 15 mL of anhydrous ethyl ether was added dropwise to an ice-cold suspension of 0.025 g (0.65 mmol) of lithium aluminum hydride in 15 mL of anhdrous ethyl ether and the mixture stirred for 30 minutes. The reaction was carefully quenched at 0° C. with 0.025 mL of water, 0.025 mL of 15% sodium hydroxide, and 0.075 mL of water. The precipiate which formed was filtered through Celite, the filtrate concentrated in vacuo, and purification of the residue by flash silica gel chromatography with 95:5 ethyl acetate:methanol gave 0.075 g (63%) of the title compound. Mp (.HCl) 145–147° C. HRMS calc'd for $C_{20}H_{26}FN_4O_2$ (MH+): 373.2040, found: 373.2054.

EXAMPLE 21

(7S,8aS)-7-(3-(Hydroxymethyl)phenoxy)methyl-2-(5-fluoropyrimidin-2-yl)-1,2,3,4,6,7,8,8a-octahydro-pyrrolo[1,2-a]pyrazine

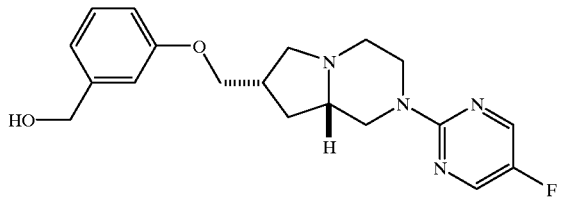

A solution of 0.15 g (0.39 mmol) of (7S,8aS)-7-(3-(methoxycarbonyl)phenoxy)methyl-2-(5-fluoropyrimidin-2-yl)-1,2,3,4,6,7,8,8a-octahydro-pyrrolo[1,2-a]pyrazine (Example 11j) in 15 mL of anhydrous ethyl ether was added dropwise to an ice-cold suspension of 0.029 g (0.78 mmol) of lithium aluminum hydride in 15 mL of anhdrous ethyl ether and the mixture stirred for 30 min. The reaction was carefully quenched at 0° C. with 0.029 mL of water, 0.029 mL of 15% sodium hydroxide, and 0.087 mL of water. The precipitate which formed was filtered through Celite, the filtrate concentrated in vacuo, and purification of the residue by flash silica gel chromatography with 95:5 chloroform:methanol gave 0.099 g (72%) of the title compound. Mp (.HCl) 85–89° C. HRMS calc'd for $C_{19}H_{24}FN_4O_2$ (MH+): 359.1883, found: 359.1895.

EXAMPLE 22

(7S,8aS)-7-(4-(2-Hydroxyethyl)phenoxy)methyl-2-(5-chloropyridin-2-yl)-1,2,3,4,6,7,8,8a-octahydro-pyrrolo[1,2-a]pyrazine A solution of 0.15 g (0.33 mmol) of (7S,8aS)-7-(4-((methoxycarbonyl)methyl)phenoxy)methyl-2-(5-chloropyridin-2-yl)-1,2,3,4,6,7,8,8a-octahydro-pyrrolo[1,2-a]pyrazine (Example 13d) in 15 mL of anhydrous ethyl ether was added dropwise to an ice-cold suspension of 0.027 g (0.65 mmol) of lithium aluminum hydride in 15 mL of anhdrous ethyl ether and the mixture stirred for 30 minutes. The reaction was carefully quenched at 0° C. with 0.027 mL of water, 0.027 mL of 15% sodium hydroxide, and 0.081 mL of water. The precipiate which formed was filtered through Celite, the filtrate concentrated in vacuo, and purification of the residue by flash silica gel chromatography with 95:5 chloroform:methanol gave 0.13 g (95%) of the title compound. Mp (.HCl) 199–202° C. HRMS calc'd for $C_{21}H_{27}ClN_3O_2$ (MH+): 388.1792, found: 388.1807.

EXAMPLE 23

(7S,8aS)-7-(4-Fluorophenoxy)methyl-2-(6-chloropyrazin-2-yl)-1,2,3,4,6,7,8,8a-octahydro-pyrrolo[1,2-a]pyrazine A mixture of 0.500 g (2.00 mmol) of (7SR,8aSR)-7-(4-fluorophenoxy)methyl-1,2,3,4,6,7,8,8a-octahydro-pyrrolo[1,2-a]pyrazine (Preparation 3), 1.49 g (10.0 mmol) of 2,6-dichloropyrazine, and 0.508 g (4.79 mmol) of sodium carbonate in 50 mL of isoamyl alcohol was heated to reflux for 16 hours. The reaction was cooled to ambient temperature, the solvent removed in vacuo, the residue taken up in ethyl acetate and water, the pH was adjusted to 11 with sodium carbonate and the layers were separated. The aqueous phase was extracted with ethyl acetate, and the combined organic layers were dried (magnesium sulfate), filtered and evaporated. Purification by flash silica gel chromatography with 90:10 ethyl acetate:hexane gave 0.491 g (68%) of the title compound. Mp (.HCl) 209–212° C. HRMS calc'd for $C_{18}H_{21}ClFN_4O$ (MH+): 363.1388, found: 363.1384.

EXAMPLE 24

(7S,8aS)-7-(4-Fluorophenoxy)methyl-2-(6-chloropyridazin-3-yl)-1,2,3,4,6,7,8,8a-octahydro-pyrrolo[1,2-a]pyrazine

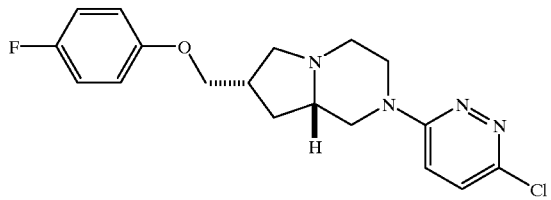

A mixture of 0.500 g (2.00 mmol) of (7SR,8aSR)-7-(4-fluorophenoxy)methyl-1,2,3,4,6,7,8,8a-octahydro-pyrrolo[1,2-a]pyrazine (Preparation 3), 1.49 g (10.0 mmol) of 3,6-dichloropyridazine, and 0.508 g (4.79 mmol) of sodium carbonate in 50 mL of isoamyl alcohol was heated to reflux for 48 hours. The reaction was cooled to ambient temperature, the solvent removed in vacuo, the residue taken up in ethyl acetate and water, the pH was adjusted to 11 with sodium carbonate and the layers were separated. The aqueous phase was extracted with ethyl acetate, and the combined organic layers were dried (magnesium sulfate), filtered and evaporated. Purification by flash silica gel chromatography with 90:10 ethyl acetate:hexane gave 0.478 g (66%) of the title compound. Mp (.HCl) 229° C. (dec). HRMS calc'd for $C_{18}H_{21}ClFN_4O$ (MH+): 363.1388, found: 363.1404.

PREPARATION 1

7-Hydroxymethyl-2-phenylmethyl-1,2,3,4,6,7,8,8a-octahydro-pyrrolo[1,2-a]pyrazine

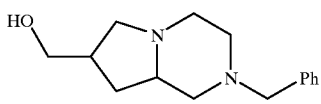

A suspension of 3.20 g (84.3 mmol) of lithium aluminum hydride in 30 mL of dry THF was cooled to 0° C. and treated dropwise with a solution of 8.00 g (27.7 mmol) of 7-methoxycarbonyl-2-phenylmethyl-1,2,3,4,6,7,8,8a-octahydro-pyrrolo[1,2-a]pyrazin-1-one (Jones, R. C. F., Howard, K. J., *J. Chem. Soc., Perkin Trans.* 1, 1993, 2391) in 80 mL of dry THF. After 30 min the reaction was carefully quenched with 3 mL of water, 3 mL of 15% NaOH and 9 of mL water. The mixture was filtered, the filtrate evaporated, the residue taken up in ethyl acetate and washed with brine. The organic layer was dried (magnesium sulfate), filtered, and evaporated to give 6.09 g (89%) of the title compound as a mixture of (7RS,8aSR)- and (7SR,8aSR)-isomers of sufficient purity for use in the next reaction (Preparation 2). m/z (MH+) 247.

PREPARATION 2

(7RS,8aSR)- and (7SR,8aSR)-7-(4-Fluorophenoxy)methyl-2-phenylmethyl-1,2,3,4,6,7,8,8a-octahydro-pyrrolo[1,2-a]pyrazine

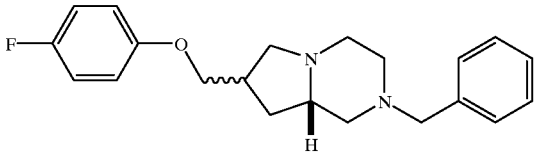

A solution of 6.00 g (24.35 mmol) of 7-hydroxymethyl-2-phenylmethyl-1,2,3,4,6,7,8,8a-octahydro-pyrrolo[1,2-a]pyrazine (Preparation 1), 4.10 g (36.5 mmol) of 4-fluorophenol and 7.70 g (29.4 mmol) of triphenylphosphine in 50 mL dry THF at 0° C. was treated dropwise with 4.6 mL (29.3 mmol) of diethyl azodicarboxylate. The reaction was allowed to warm to room temperature and stirred for 24 hours. The solvent was evaporated, the residue taken up in ethyl acetate and washed with 1M NaOH (3×). The organic layer was dried (magnesium sulfate), filtered, and evaporated to give the crude product as a dark oil. Purification by flash silica gel chromatography eluting with 95:5 ethyl acetate:methanol gave 2.27 g (27%) of the (7RS,8aSR)-isomer and 0.410 g (5%) of the (7SR,8aSR)-isomer.

(7RS,8aSR)-7-(4-fluorophenoxy)methyl-2-phenylmethyl-1,2,3,4,6,7,8,8a-octahydro-pyrrolo[1,2-a]pyrazine: $^{13}C$ NMR (CDCl$_3$): δ 32.0, 35.5, 51.5, 52.5, 56.4, 57.7, 62.7, 62.9, 72.7, 115.45, 115.55, 115.86, 127.0, 128.2, 129.2, 138.3, 155.1, 155.6, 158.8.

(7SR,8aSR)-7-(4-fluorophenoxy)methyl-2-phenylmethyl-1,2,3,4,6,7,8,8a-octahydro-pyrrolo[1,2-a]pyrazine: $^{13}C$ NMR (CDCl$_3$): δ 31.6, 35.4, 51.6, 52.5, 57.4, 57.6, 61.7, 62.9, 71.6, 115.40, 115.51, 115.60, 115.91, 127.0, 128.2, 129.2, 138.2, 155.13, 155.15, 155.7, 158.8.

PREPARATION 3

(7SR,8aSR)-7-(4-Fluorophenoxy)methyl-1,2,3,4,6,7,8,8a-octahydro-pyrrolo[1,2-a]pyrazine

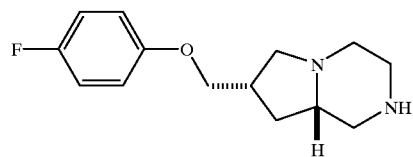

A mixture of 1.20 g (3.53 mmol) of (7SR,8aSR)-7-(4-fluorophenoxy)methyl-2-phenylmethyl-1,2,3,4,6,7,8,8a-octahydro-pyrrolo[1,2-a]pyrazine (Preparation 2), 30 mL of methanol and 2.5 mL of 5.0 M ammonium formate was treated with an aqueous slurry of 0.15 g of 10% palladium on carbon. The mixture was heated at reflux for 48 hours, cooled to ambient temperature, filtered through Celite, and the filtrate was evaporated. The residue was taken up in dilute aqueous ammonium hydroxide and extracted with chloroform (3×). The combined organic phase was dried (magnesium sulfate), filtered and evaporated to give 0.874 g (99%) of the title compound. $^{13}C$ NMR (CDCl$_3$): δ 32.0, 34.5, 45.2, 50.9, 53.4, 57.0, 63.7, 72.6, 115.4, 115.5, 115.8, 155.1, 155.6, 158.7. HRMS calc'd for $C_{14}H_{20}FN_2O$ (MH+): 251.156, found: 251.155.

PREPARATION 4

(7RS,8aSR)-7-Hydroxymethyl-7-methyl-2-phenylmethyl-1,2,3,4,6,7,8,8a-octahydro-pyrrolo[1,2-a]pyrazine

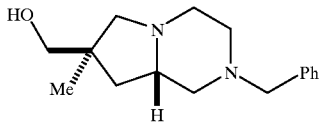

A solution of 3.33 g (11 mmol) of (7RS,8aSR)-7-methoxycarbonyl-7-methyl-2-phenyl-methyl-1,2,3,4,6,7,8,8a-octahydro-pyrrolo[1,2-a]pyrazin-1-one (Jones, R. C. F., Howard, K. J., *J. Chem. Soc., Perkin Trans.* 1, 1993, 2391) in 125 mL of dry THF was added dropwise to a stirred suspension of 1.26 g (33 mmol) of lithium aluminum hydride in 125 mL of dry THF. The solution was stirred for 2 hours at room temperature, and carefully quenched with 1.26 mL of water, 1.26 mL of 15% NaOH, and 3.78 mL of water. After stirring for 30 minutes, the mixture was filtered through Celite, dried (magnesium sulfate), filtered and evaporated. Purification by flash silica gel chromatography eluting with 9:1 chloroform:methanol gave 1.67 g (58%) of the title compound. $^{13}$C NMR (base, CDCl$_3$): δ 25.3, 39.7, 41.8, 51.1, 51.6, 57.1, 62.3, 62.9, 63.3, 71.3, 127.0, 128.2, 128.7, 129.2, 138.3. m/z (MH+) 261.

PREPARATION 5

(7RS,8aSR)-7-Hydroxymethyl-7-methyl-2-(5-fluoropyrimdin-2-yl)-1,2,3,4,6,7,8,8a-octahydro-pyrrolo[1,2-a]pyrazine

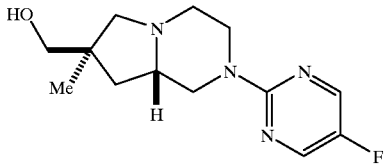

A solution of 1.65 g (6.35 mmol) of (7RS,8aSR)-7-hydroxymethyl-7-methyl-2-phenylmethyl-1,2,3,4,6,7,8,8a-octahydro-pyrrolo[1,2-a]pyrazine (Preparation 4) in 20 mL of methanol was mixed with 4.44 mL (22.2 mmol) of 5M aqueous ammonium formate, an aqueous slurry of 0.825 g of 10% palladium on carbon was added and the mixture was stirred at ambient temperature overnight. The solution was filtered through Celite and evaporated to give (7RS,8aSR)-7-hydroxymethyl-7-methyl-1,2,3,4,6,7,8,8a-octahydro-pyrrolo[1,2-a]pyrazine of sufficient purity for use in the next step.

A mixture of (7RS,8aSR)-7-hydroxymethyl-7-methyl-1,2,3,4,6,7,8,8a-octahydro-pyrrolo[1,2-a]pyrazine (1.08 g, 6.35 mmol), 0.925 g (6.98 mmol) of 2-chloro-5-fluoropyrimidine (Dunaiskis, A. et., *Org. Prep. Proc. Int.*, 1995, 27, 600–602), and 1.48 g (13.96 mmol) of sodium carbonate and 65 mL of water was heated at 90° C. for 72 hours. The solution was cooled and extracted with chloroform (3×). The combined organic layers were dried (magnesium sulfate), filtered and evaporated. Purification by flash silica gel chromatography eluting with chloroform:methanol (95:5) gave 0.80 g (47%) of the title compound. $^{13}$C NMR (CDCl$_3$): δ 25.5, 39.5, 41.7, 43.3, 48.7, 51.2, 62.3, 63.8, 71.0, 144.9, 145.2, 149.8, 153.1, 158.9. m/z (MH+) 267.

PREPARATION 6

(7R,8aS)-7-Hydroxy-2-(5-fluoropyrimidin-2-yl)-1,2,3,4,6,7,8,8a-octahydro-pyrrolo[1,2-a]pyrazine

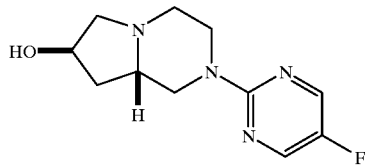

Step A

A solution of 9.75 g (42.0 mmol) of (7R,8aS)-7-hydroxy-2-phenylmethyl-1,2,3,4,6,7,8,8a-octahydro-pyrrolo[1,2-a]pyrazine (Diafi, L. et al., *J. Het. Chem.*, 1990, 27, 2181) and 29.4 mL of 5M ammonium formate in 140 mL of methanol was treated with an aqueous slurry of 4.9 g of 10% palladium on carbon and the mixture was stirred at ambient temperature for 18 hours. The mixture was filtered through Celite and evaporated to give (7R,8aS)-7-hydroxy-1,2,3,4,6,7,8,8a-octahydro-pyrrolo[1,2-a]pyrazine as a clear oil.

Step B

A mixture of the crude (7R,8aS)-7-hydroxy-1,2,3,4,6,7,8,8a-octahydro-pyrrolo[1,2-a]-pyrazine, 9.96 g (52.5 mmol) of 2-chloro-5-fluoropyrimidine (Dunaiskis, A. et al., *Org. Prep. Proc. Int.*, 1995, 27, 600–602), 13.4 g (126 mmol) of sodium carbonate and 450 mL of water was heated at 95° C. for 72 hours. The mixture was cooled, extracted with chloroform (2×), and the combined organic phase was dried (magnesium sulfate), filtered and evaporated. Purification by flash silica gel chromatography with 95:5 ethyl acetate:methanol gave 8.54 g (85%) of the title compound. $^{13}$C NMR (base, CDCl$_3$): δ 39.1, 43.7, 48.7, 51.0, 60.2, 62.9, 69.4, 144.95, 145.24, 149.9, 153.2, 158.9. m/z (MH+) 239.

PREPARATION 7

(7R,8aS)-7-Methanesulfonyloxy-2-(5-fluoropyrimidin-2-yl)-1,2,3,4,6,7,8,8a-octahydro-pyrrolo[1,2-a]pyrazine

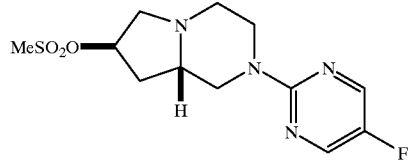

A solution of 1.00 g (4.20 mmol) of (7R,8aS)-7-hydroxy-2-(5-fluoropyrimidin-2-yl)-1,2,3,4,6,7,8,8a-octahydro-pyrrolo[1,2-a]pyrazine (Preparation 6) and 0.644 mL (4.62 mmol) of triethylamine in 40 mL of methylene chloride was chilled to 0° C. and 0.34 mL (4.41 mmol) of methanesulfonyl chloride in 20 mL of methylene chloride was added slowly. After 30 minutes, water was added and the pH adjusted to 10 with 1M NaOH. The layers were separated, the organic phase was washed with water (2×), dried (magnesium sulfate), filtered and evaporated to give 1.15 g (86%) of the title compound of sufficient purity for use in subsequent reactions. m/z (MH+) 317.

PREPARATION 8

7-Methoxycarbonyl-2-phenylmethyl-1,2,3,4,8,8a-hexahydro-pyrrolo[1,2-a]pyrazin-1-one

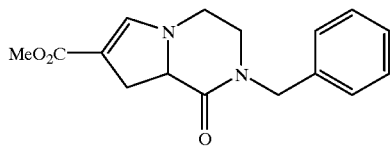

A solution of 8.6 g (27 mmol) of dimethyl 2-phenylmethyl-2,3,5,6,7,7a-hexahydro-1H-pyrrolo[1,2-c]imidazol-5,7-dioate (Jones, R. C. F., Howard, K., J. *J. Chem. Soc. Perkin Trans.* 1, 1993, 2391) and 2.0 mL (13 mmol) of 1,8-diazabicyclo[5.4.0]undec-7-ene (DBU) in 150 mL of methanol was heated at reflux for 16 hours. The solvent was evaporated, the residue was dissolved in ethyl acetate and washed with water (2x), dried (magnesium sulfate), filtered and evaporated to give 6.45 g (84%) of the title compound. $^{13}$C NMR (CDCl$_3$): δ 32.9, 43.9, 45.6, 50.5, 50.8, 63.1, 106.0, 127.7, 128.0, 128.8, 136.2, 148.1, 165.7, 170.0. HRMS calc'd for C$_{16}$H$_{19}$N$_2$O$_3$ (MH+): 287.1396, found: 287.1406.

PREPARATION 9

(7SR,8aSR)-7-Methoxycarbonyl-2-phenylmethyl-1,2,3,4,6,7,8,8a-octahydro-pyrrolo[1,2-a]pyrazin-1-one

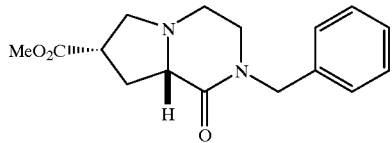

A mixture of 40.0 g (140 mmol) of 7-methoxycarbonyl-2-phenylmethyl-1,2,3,4,8,8a-hexahydro-pyrrolo[1,2-a]pyrazin-1-one (Preparation 8) and 10 g of 5% Pd on charcoal in 600 mL of ethyl acetate was shaken in a Parr apparatus under 50 psi of hydrogen gas for 6.5 hours. The mixture was filtered through Celite, and the filtrate was evaporated to give 38.4 g (95%) of the title compound. $^{13}$C NMR (CDCl$_3$): δ 31.8, 41.4, 44.8, 46.5, 49.6, 52.1, 55.2, 64.0, 127.5, 128.1, 128.7, 128.8, 136.6, 169.6, 174.8. HRMS calc'd for C$_{16}$H$_{22}$N$_2$O$_3$ (MH+): 289.1552, found: 289.1549.

PREPARATION 10

(7SR,8aSR)-7-Hydroxymethyl-2-phenylmethyl-1,2,3,4,6,7,8,8a-octahydro-pyrrolo[1,2-a]pyrazine

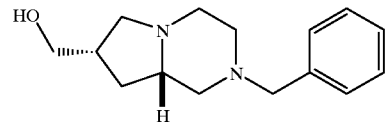

A three-neck flask fitted with a reflux condenser and dropping funnel was charged with 100 mL of dry THF and 2.4 g (63 mmol) of lithium aluminum hydride (LAH), and a solution of 6.0 g (21 mmol) of (7SR,8aSR)-7-methoxycarbonyl-2-phenylmethyl-1,2,3,4,6,7,8,8a-octahydro-pyrrolo[1,2-a]pyrazin-1-one (Preparation 9) in 60 mL of dry THF was placed in the dropping funnel. The LAH suspension was heated to reflux and the ester solution was added over a 30–60 minutes period. Reflux continued for another 4 hours, the reaction was cooled in an ice bath and quenched by careful addition of 2.4 mL of water, 2.4 mL of 15% sodium hydroxide, and 7.2 mL of water. Stirring continued until a white precipitate formed, the mixture was filtered through Celite, and the filtrate was evaporated to give 5.0 g (97%) of the title compound of sufficient purity for use in subsequent reactions. $^{13}$C NMR (CDCl$_3$): δ 31.1, 37.2, 51.3, 52.6, 57.4, 62.8, 62.9, 67.4, 127.0, 128.2, 129.2, 138.2. HRMS calc'd for C$_{15}$H$_{23}$N$_2$O (MH+) 247.1810, found: 247.1800.

PREPARATION 11

(7S,8aS)-7-Methoxycarbonyl-1,2,3,4,6,7,8,8a-octahydro-pyrrolo[1,2-a]pyrazin-1-one

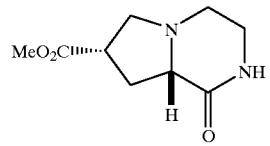

A mixture of 77.3 g (16 mmol) of N-benzyloxycarbonyl-cis-4-carboxy-L-proline dimethyl ester (Bridges, R. J. et al., *J. Med. Chem.*, 1991, 34, 717) and 169 mL (55 mmol) of 5M ammonium formate in 1000 mL of methanol was treated with an aqueous slurry of 15.5 g of 10% palladium on carbon. After 4 hours, the mixture was filtered through Celite, the filtrate was concentrated to about 500 mL, saturated with sodium bicarbonate, and extracted with chloroform (5x). The aqueous layer was saturated with sodium chloride and extracted with chloroform (3x). The combined organic phase was dried (magnesium sulfate), filtered and evaporated to give 39.8 g (88%) of cis-4-carboxy-L-proline dimethyl ester.

A mixture of 39.8 g (213 mmol) of cis-4-carboxy-L-proline dimethyl ester, 40.2 g (213 mmol) of 2-(phthalimido)acetaldehyde (Preparation 12), and 17.5 g (213 mmol) of anhydrous sodium acetate in 2150 mL of dry methylene chloride was treated with 67.7 g (319 mmol) of sodium (triacetoxy)borohydride in small portions over a 1 hour period. The solution was stirred for 16 hours, water was added, and the pH adjusted to 10 with 1M sodium hydroxide. The organic phase was separated, dried (magnesium sulfate), filtered and evaporated to give 73.8 g (96%) of N-(2-(phthalimido)ethyl-cis-4-carboxy-L-proline dimethyl ester.

A solution of 73.8 g (205 mmol) of N-(2-(phthalimido)ethyl-cis-4-carboxy-L-proline dimethyl ester and 44.1 mL (513 mmol) of 40% aqueous methyl amine in 3100 mL of methanol was stirred at ambient temperature for 16 hours. The solvent was evaporated and the crude product purified by flash silica gel chromatography starting with 4:1 diethyl ether:methanol and ending with 2:1 diethyl ether: methanol to give 37.0 g (91%) of the title compound of sufficient purity for use in subsequent reactions. m/z (MH+) 199.

Another sample of the title compound was purified further by flash silica gel chromatography with ethyl ether:methanol (9:1 to 8:2) and formed a white solid on standing. Mp 70–74° C. $^{13}$C NMR (d$_6$-DMSO): δ 32.2, 40.5, 42.4, 46.6, 52.6, 55.8, 64.0, 173.9, 176.2. HRMS calc'd for $C_9H_{15}N_2O_3$ (MH+):199.1083, found: 199.1091.

PREPARATION 12

2-(Phthalimido)acetaldehyde

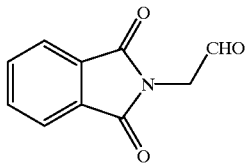

A solution of 50.0 g (190 mmol) of 2-(phthalimido) acetaldehyde diethyl acetal in 300 mL of toluene was treated with 150 mL of 50% aqueous trifluoroacetic acid and the mixture was stirred vigorously at ambient temperature for 72 hours. The solution was concentrated in vacuo and 100 mL of ethyl acetate was added. The white precipitate was filtered off and washed with ice-cold ethyl acetate (100 mL) to give 30.0 g (78%) of the title compound.

PREPARATION 13

(7S,8aS)-7-Hydroxymethyl-2-(5-fluoropyrimidin-2-yl )-1,2,3,4,6,7,8, 8a -octahydro-pyrrolo[1,2-a] pyrazine

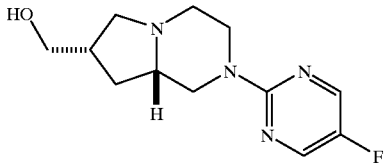

Step A

A solution of 1.75 g (8.84 mmol) of (7S,8aS)-7-methoxycarbonyl-1,2,3,4,6,7,8,8a-octahydro-pyrrolo[1,2-a] pyrazin-1-one (Preparation 11) in 100 mL of THF was added dropwise to a suspension of 0.67 g (18 mmol) of lithium aluminum hydride in 100 mL of refluxing tetrahydrofuran (THF). After stirring for 1 hour, the solution was cooled and carefully quenched with 0.67 mL of water, 0.67 mL of 15% sodium hydroxide, and 2.0 mL of water. The precipitate was filtered and the filtrate was concentrated to give 1.4 g of (7S,8aS)-7-hydroxymethyl-1,2,3,4,6,7,8,8a-octahydro-pyrrolo[1,2-a]pyrazine of sufficient purity for use in subsequent reactions.

Step B

A mixture of 1.38 g (8.84 mmol) of (7S,8aS)-7-hydroxymethyl-1,2,3,4,6,7,8,8a-octahydro-pyrrolo[1,2-a] pyrazine, 1.30 g (9.87 mmol) of 2-chloro-5-fluoropyrimidine (Dunaiskis, A. et al., Org. Prep. Proc. Int., 1995, 27, 600–602), and 2.85 g (26.9 mmol) of sodium carbonate and 90 mL of water was heated at 95° C. for 16 hours. The solution was cooled and extracted with chloroform (2x), the combined organic phase was dried (magnesium sulfate), filtered and evaporated. Purification by flash silica gel chromatography with 9:1 chloroform:methanol gave 0.97 g (43%) of the title compound. Mp 123–124° C. m/z (MH+) 253. $^{13}C$ NMR (CDCl$_3$): δ 30.9, 37.1, 43.8, 48.8, 51.3, 57.5, 62.6, 67.2, 144.9, 145.2, 149.9, 153.2, 158.8.

PREPARATION 14

(7S,8aS)-7-Hydroxymethyl-2-(5-chloropyridin-2-yl)-1,2,3,4,6,7,8,8a-octahydro-pyrrolo[1,2-a] pyrazine

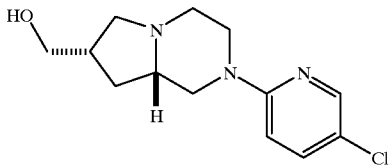

A mixture of 0.50 g (3.2 mmol) of (7S,8aS)-7-hydroxymethyl-1,2,3,4,6,7,8,8a-octahydro-pyrrolo[1,2-a] pyrazine (Preparation 13, Step A), 2.37 g (16.0 mmol) of 2,5-dichloropyridine, 0.85 g (8.0 mmol) of sodium carbonate and 35 mL of isoamyl alcohol was refluxed for 48 hours. The hot solution was filtered and the filtrate evaporated. Purification by flash silica gel chromatography with 9:1 chloroform:methanol gave 0.25 g (29%) of the title compound. $^{13}C$ NMR (CDCl$_3$): d 31.1, 37.3, 44.7, 49.7, 51.2, 57.2, 62.5, 66.9, 107.9, 119.9, 137.1, 146.1, 157.6. m/z (MH+) 268.

PREPARATION 15

(7S,8aS)-7-Hydroxy-2-(5-fluoropyrimidin-2-yl)-1,2,3,4,6,7,8,8a-octahydro-pyrrolo[1,2-a]pyrazine

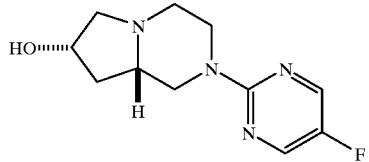

A solution of 1.58 g (4.61 mmol) of (7S,8aS)-2-(5-fluoropyrimidin-2-yl)-1,2,3,4,6,7,8,8a-octahydro-pyrrolo[1,2-a]pyrazin-7-yl benzoate (Example 9) in 200 mL of methanol was treated with 50 mL of 15% aqueous sodium hydroxide. After 30 minutes, the solvent was removed and the residue partitioned between water and ethyl acetate. The layers were separated, the organic phase was dried (magnesium sulfate), filtered and evaporated to give 0.922 g (84%) of the title compound. $^{13}C$ NMR (CDCl$_3$): δ 39.4, 43.7, 49.0, 51.2, 62.2, 63.6, 69.9, 144.9, 145.2, 149.9, 153.2,158.9. m/z (MH+) 239.

PREPARATION 16

(7S,8aS)-7-Hydroxymethyl-2-(4-cyanophenyl)-1,2,3,4,6,7,8,8a-octahydro-pyrrolo[2-a]pyrazine

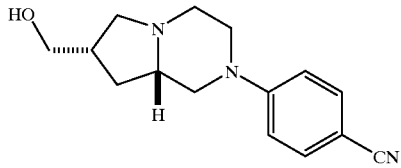

A mixture of 1.5 g (9.6 mmol) of (7S,8aS)-7-hydroxymethyl-1,2,3,4,6,7, 8,8a-octahydro-pyrrolo[1,2-a]

pyrazine (Preparation 13, Step A), 1.75 g (14.4 mmol) of 4-fluorobenzonitrile and 2.04 g (1 9.2 mmol) of sodium carbonate in 10 mL of DMSO was heated at 80° C. for 16 hours. The solution was cooled to room temperature, diluted with water and extracted with 1:1 ethyl acetate:diethyl ether (3×). The combined organic phase was dried (magnesium sulfate), filtered and evaporated. Purification by flash silica gel chromatography with 9:1 chloroform: methanol gave 0.925 g (37%) of the title compound. $^{13}$C NMR (CDCl$_3$): δ 31.1, 37.2, 46.7, 51.0, 51.8, 57.6, 62.3, 67.3, 100.1, 114.3, 120.0, 133.5, 153.4. m/z (MH+) 258.

PREPARATION 17

(7R,8aS)-7-Hydroxy-2-(5-chloropyridin-2-yl)-1,2,3,4,6,7,8,8a-octahydro-pyrrolo[1,2-a]pyrazine

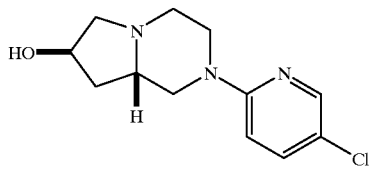

A mixture of 3.81 g (26.8 mmol) of (7R,8aS)-7-hydroxy-1,2,3,4,6,7,8,8a-octahydro-pyrrolo[1,2-a]pyrazine (Preparation 6, Step A), 19.8 g (134 mmol) of 2,5-dichloropyridine, 7.10 g (67.0 mmol) of sodium carbonate and 275 mL of isoamyl alcohol was heated at reflux for 72 hours. The mixture was cooled to about 100° C., filtered hot, and the filtrate concentrated in vacuo. Purification of the residue by flash silica gel chromatography with 9:1 chloroform:methanol gave 0.63 g (9%) of the title compound of sufficient purity for use in subsequent reactions. m/z (MH+) 254.

PREPARATION 18

(7S,8aS)-7-Hydroxy-2-(5-chloropyridin-2-yl)-1,2,3,4,6,7,8,8a-octahydro-pyrrolo[1,2-a]pyrazine

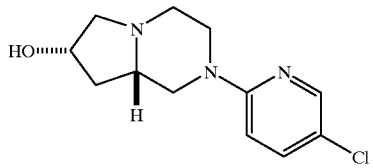

A solution of 0.52 g (1.45 mmol) of (7S,8aS)-2-(5-chloropyridin-2-yl)-1,2,3,4,6,7,8,8a-octahydro-pyrrolo[1,2-a]pyrazin-7-yl benzoate (Example 17) in 50 mL of methanol was treated with 50 mL of 15% aqueous sodium hydroxide and stirred at ambient temperature for 30 minutes. The solent was concentrated by half in vacuo and the residue extracted with chloroform (3×). The combined organic phase was dried (magnesium sulfate), filtered and evaporated Purification by flash silica gel chromatography with 9:1 chloroform:methanol gave 0.25 g (68%) of the title compound. Mp (base) 167–168° C. m/z (MH+) 254.

What is claimed is:

1. A method of treating a disorder or condition that can be treated by altering serotonin mediated neurotransmission in a mammal, comprising administering to such mammal an amount of a compound of formula I

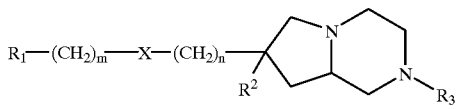

wherein R$_1$ is phenyl, naphthyl, benzoxazolonyl, indolyl, indolonyl, benzimidazolyl, quinolyl, furyl, benzofuryl, thienyl, benzothienyl, oxazolyl, benzoxazolyl;

R$_2$ is H or (C$_1$–C$_6$)alkyl;

R$_3$ is phenyl, pyridinyl, pyrimidinyl, pyrazinyl, or pyridazinyl;

R$_4$ is H or (C$_1$–C$_6$)alkyl;

R$_5$ is H or (C$_1$–C$_6$)alkyl;

wherein each group of R$_1$ and R$_3$ may be independently and optionally substituted with one to four substituents independently selected from the groups consisting of fluoro, chloro, bromo, iodo, cyano, nitro, thiocyano, —SR$_4$, —SOR$_4$, —SO$_2$R$_4$, —NHSO$_2$R$_4$, —(C$_1$–C$_6$)alkoxy, —NR$_4$R$_5$, —NR$_4$COR$_5$, —CONR$_4$R$_5$, phenyl, —COR$_4$, —COOR$_4$, —(C$_1$–C$_6$)alkyl, —(C$_1$–C$_6$)alkyl substituted one to six halogens, —(C$_3$–C$_6$)cycloalkyl, and trifluoromethoxy;

X is O, S, SO, SO$_2$, NR$_4$, C=O, CH(OH), CHR$_4$,

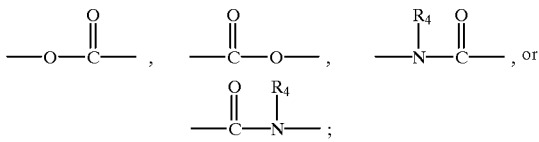

m is 0, 1 or 2;

n is 0, 1 or 2;

or a pharmaceutically acceptable salt thereof;

that is effective in treating such disorder or condition.

2. A method according to claim 1, wherein the compound of formula I or pharmaceutically acceptable salt that is employed is one wherein R$_1$ is phenyl, naphthyl, benzoxazolonyl, indolyl, indolonyl, benzimidazolyl, or quinolyl; and wherein R$_1$ and R$_3$ may be independently substituted with up to three substituents independently selected from the group consisting of fluoro, chloro, bromo, iodo, cyano, —NR$_4$R$_5$, —(C$_1$–C$_6$)alkoxy, —COOR$_4$, —CONR$_4$R$_5$, —(C$_1$–C$_6$)alkyl, —(C$_1$–C$_6$)alkyl substituted with one to six halogens, —(C$_3$–C$_6$)cycloalkyl, and trifluoromethoxy;

R$_2$ is H or CH$_3$;

X is O, C=O, CHOH, —C(=O)O—, or CH$_2$;

m is 0 or 1; and n is 0 or 1.

3. A method according to claim 2, wherein the compound of formula I or pharmaceutically acceptable salt that is employed is one wherein R$_1$ is phenyl or substituted phenyl;

R$_3$ is substituted or unsubstituted phenyl, pyridinyl, or pyrimidinyl; and

X is O, —C(=O)O—, or CH$_2$.

4. A method according to claim 3, wherein the compound of formula I or pharmaceutically acceptable salt that is employed is one wherein $R_2$ is H;

X is O;

m is 0; and n is 1.

5. A method according to claim 4, wherein the compound of formula I or pharmaceutically acceptable salt that is employed is one wherein $R_1$ is fluorophenyl, cyanophenyl or (trifluoromethyl) phenyl; and $R_3$ is chloropyridinyl.

6. A method according to claim 4, wherein the compound of formula I or pharmaceutically acceptable salt that is employed is one wherein $R_1$ is fluorophenyl, cyanophenyl or (trifluoromethyl) phenyl; and $R_3$ is fluropyrimidinyl.

7. A method according to claim 5, wherein the compound of formula I or pharmaceutically acceptable salt that is employed is one wherein $R_3$ is 5-chloro-2-pyridinyl.

8. A method according to claim 6, wherein the compound of formula I or pharmaceutically acceptable salt that is employed is one wherein $R_3$ is 5-fluoro-2-pyrimidinyl.

9. A method according to claim 1, wherein the compound of formula I or pharmaceutically acceptable salt that is employed is one of the following compounds or a pharmaceutically acceptable salt thereof:

(7S,8aS)-7-(4-fluorophenoxy)methyl-2-(5-chloropyridin-2-yl)-1,2,3,4,6,7,8,8a-octahydro-pyrrolo[1,2-a]pyrazine;

(7S,8aS)-7-(3-cyanophenoxy)methyl-2-(5-chloropyidin-2-yl)-1,2,3,4,6,7,8,8a-octahydro-pyrrolo[1,2-a]pyrazine;

(7S,8aS)-7-(4-fluorophenoxy)methyl-2-(5-fluoropyrimidin-2-yl)-1,2,3,4,6,7,8,8a-octahydro-pyrrolo[1,2-a]pyrazine;

(7S,8aS)-7-(3-(trifluoromethyl)phenoxy)methyl-2-(5-fluoropyrimidin-2-yl)-1,2,3,4,6,7,8,8a-octahydro-pyrrolo[1,2-a]pyrazine;

(7S,8aS)-7-(3-cyanophenoxy)methyl-2-(5-fluoropyrimidin-2-yl)-1,2,3,4,6,7,8,8a-octahydro-pyrrolo[1,2-a]pyrazine; or (7S,8aS)-7-(4-cyanophenoxy)methyl-2-(5-fluoropyrimidin-2-yl)-1,2,3,4,6,7,8,8a-octahydro-pyrrolo[1,2-a]pyrazine.

10. A method of treating a disorder or condition that can be treated by altering serotonin mediated neurotransmission in a human, comprising administering to said human an amount of a compound of the formula I, as defined in claim 1, or a pharmaceutically acceptable salt thereof, that is effective in treating or preventing such disorder or condition.

11. A method of treating migraine, headache or cluster headache in a mammal comprising administering to said mammal an amount of a compound of the formula I, as defined in claim 1, or a pharmaceutically acceptable salt thereof, that is effective in treating such disorder.

12. A method of treating a disorder selected from anxiety, depression, dysthymia, major depressive disorder, panic disorder, obsessive-compulsive disorder, posttraumatic stress disorder, avoidant personality disorder, borderline personality disorder and phobias in a mammal, comprising administering to said mammal an amount of a compound of the formula I, as defined in claim 1, or a pharmaceutically acceptable salt thereof, that is effective in treating such disorder.

13. A method of treating a disorder of cognition, memory or learning, or Alzheimer's disease in a mammal, comprising administering to said mammal an amount of a compound of the formula I, as defined in claim 1, or a pharmaceutically acceptable salt thereof, that is effective in treating such disorder.

14. A method of treating anxiety or depression associated with senile dementia or Alzheimer's disease in a mammal, comprising administering to said mammal an amount of a compound of the formula I, as defined in claim 1, or a pharmaceutically acceptable salt thereof, that is effective in treating such disorder.

15. A method of treating prostate cancer in a mammal, comprising administering to said mammal an amount of a compound of the formula I, as defined in claim 1, or a pharmaceutically acceptable salt thereof, that is effective in treating such disorder.

16. A method of treating cerebral infarct caused by stroke, ischemia or traumatic head injury in a mammal, comprising administering to said mammal an amount of a compound of the formula I, as defined in claim 1, or a pharmaceutically acceptable salt thereof, that is effective in treating such disorder.

17. A method according to claim 16, wherein the compound of formula I, or pharmaceutically acceptable salt thereof, is administered in combination with a $5HT_2$ antagonist, or a pharmaceutically acceptable salt thereof.

18. A method of treating a sexual disorder in a mammal, comprising administering to said mammal an amount of a compound of the formula I, as defined in claim 1, or a pharmaceutically acceptable salt thereof, that is effective in treating such disorder.

19. A method of treating dizziness in a mammal, comprising administering to said mammal an amount of a compound of the formula I, as defined in claim 1, or a pharmaceutically acceptable salt thereof, that is effective in treating such disorder.

20. A method of treating an eating disorder in a mammal, comprising administering to said mammal an amount of a compound of the formula I, as defined in claim 1, or a pharmaceutically acceptable salt thereof, that is effective in treating such disorder.

21. A method of treating pain in a mammal, comprising administering to said mammal an amount of a compound of the formula I, as defined in claim 1, or a pharmaceutically acceptable salt thereof, that is effective in treating such disorder.

22. A method according to claim 12, wherein the compound of formula I or pharmaceutically acceptable salt thereof is adminstered in combination with a serotonin reuptake inhibitor.

23. A method according to claim 14, wherein the compound of formula I or pharmaceutically acceptable salt thereof is adminstered in combination with a serotonin reuptake inhibitor.

24. A method of treating attention deficit hyperactivity disorder in a mammal, comprising administering to said mammal an amount of a compound according to claim 1 that is effective in treating such disorder.

25. A method of imaging an organ in a mammal, comprising administering to said mammal a radioactive form of a compound according to claim 1, and detecting the emissions of the radioactive compound.

26. A method of imaging an organ in a mammal comprising administering to said mammal a compound according to claim 1 in combination with a radioactive agent, and detecting the emissions of the radioactive agent.

* * * * *